US010543277B2

(12) United States Patent
Antony et al.

(10) Patent No.: US 10,543,277 B2
(45) Date of Patent: Jan. 28, 2020

(54) FORMULATION OF CURCUMIN WITH ENHANCED BIOAVAILABILITY OF CURCUMIN AND METHOD OF PREPARATION AND TREATMENT THEREOF

(71) Applicant: ARJUNA NATURAL PRIVATE LIMITED, Alwaye (IN)

(72) Inventors: Benny Antony, Ankamaly (IN); Moni Abraham Kuriakose, Ernakulam (IN)

(73) Assignee: ARJUNA NATURAL PRIVATE LIMITED, Alwaye (IN)

(*) Notice: Subject to any disclaimer, the term of this patent is extended or adjusted under 35 U.S.C. 154(b) by 791 days.

(21) Appl. No.: 14/698,944

(22) Filed: Apr. 29, 2015

(65) Prior Publication Data
US 2016/0008479 A1 Jan. 14, 2016

Related U.S. Application Data

(60) Continuation of application No. PCT/IN2013/000673, filed on Oct. 31, 2013, and a continuation-in-part of application No. 14/476,555, filed on Sep. 3, 2014, now Pat. No. 10,159,654, which is a division of application No. 13/645,031, filed on Oct. 4, 2012, now Pat. No. 8,859,020, application No. 14/698,944, which is a continuation-in-part of application No. 14/623,608, filed on Feb. 17, 2015, now Pat. No. 9,878,040, and a continuation-in-part of application No. 14/520,292, filed on Oct. 21, 2014, now Pat. No. 9,861,677, and a continuation-in-part of application No. 14/206,044, filed on Mar. 12, 2014, now Pat. No. 9,492,402, said application No. 13/645,031 is a continuation-in-part of application No. PCT/IN2011/000232, filed on Apr. 4, 2011, said application No. 14/623,608 is a division of application No. 13/674,249, filed on Nov. 12, 2012, now Pat. No. 8,993,013, which is a division of application No. 13/506,572, filed on Apr. 30, 2012, now Pat. No. 8,329,233, which is a division of application No. 12/926,980, filed on Dec. 21, 2010, now Pat. No. 8,197,869, which is a division of application No. 12/073,864, filed on Mar. 11, 2008, now Pat. No. 7,883,728, which is a continuation-in-part of application No. 11/635,599, filed on Dec. 8, 2006, now Pat. No. 7,736,679, said application No. 14/520,292 is a division of application No. 13/385,717, filed on Mar. 5, 2012, now Pat. No. 8,623,431, which is a division of application No. 12/926,985, filed on Dec. 21, 2010, now Pat. No. 8,153,172, which is a division of application No. 12/662,740, filed on Apr. 30, 2010, now Pat. No. 7,879,373, which is a division of application No. 11/635,599, filed on Dec. 8, 2006, (Continued)

(30) Foreign Application Priority Data

Apr. 5, 2010 (IN) .............................. 950CHE2010
Nov. 3, 2012 (IN) ............................. 4128CHE2012

(51) Int. Cl.
*A61K 47/46* (2006.01)
*A61K 31/12* (2006.01)
*A61K 9/00* (2006.01)

(52) U.S. Cl.
CPC ............ *A61K 47/46* (2013.01); *A61K 9/0053* (2013.01); *A61K 31/12* (2013.01)

(58) Field of Classification Search
None
See application file for complete search history.

(56) References Cited

U.S. PATENT DOCUMENTS 3,340,250 A   9/1967 Sair
5,120,538 A   6/1992 Oei
(Continued)

FOREIGN PATENT DOCUMENTS

CN   1483405 A   3/2004
CN   1491089 A   4/2004
(Continued)

OTHER PUBLICATIONS

Aratanechemuge, Y, Komiya, T, Moteki, H, Katsuzaki, H, Imai, K, and Hibasami, H, Selective Induction of Apoptosis by ar-Turmerone Isolated From Turmeric (*Curcuma longa* L) in Two Human Leukemia Cell Lines, But Not in Human Stomach Cancer Cell Line, International Journal of Molecular Medicine, 9:481-484 (2002).

(Continued)

*Primary Examiner* — Amy L Clark
(74) *Attorney, Agent, or Firm* — Jyoti C Iyer

(57) ABSTRACT

A medicinal composition useful for the treatment of head and neck cancer premalignant lesions. The composition includes a curcuminoid mixture and an essential oil of turmeric. The curcuminoid mixture consists of curcumin, demethoxycurcumin and bisdemethoxycurcumin. The essential oil of turmeric includes about 45% ar-turmerone. The weight ratio of curcuminoid mixture to essential oil of turmeric ranges from about 1:3 to about 99:1. Methods of preparation of the composition is provide. Methods of treatment of head and neck cancer premalignant lesions by oral administration is provided.

8 Claims, 6 Drawing Sheets

Related U.S. Application Data now Pat. No. 7,736,679, which is a continuation of application No. PCT/IN2005/000176, filed on May 30, 2005, said application No. 14/206,044 is a continuation-in-part of application No. 13/645,031, and a continuation-in-part of application No. 13/674,249, and a continuation-in-part of application No. 14/094,725, filed on Dec. 2, 2013, now Pat. No. 8,895,087.

(60) Provisional application No. 61/794,175, filed on Mar. 15, 2013.

(56) References Cited

U.S. PATENT DOCUMENTS

| | | | |
|---|---|---|---|
| 5,536,506 | A | 7/1996 | Majeed |
| 5,861,415 | A | 1/1999 | Majeed |
| 6,224,871 | B1 | 5/2001 | Hastings |
| 6,224,877 | B1 | 5/2001 | Gaikar |
| 6,235,287 | B1 | 5/2001 | Weidner |
| 6,245,350 | B1 | 6/2001 | Amey |
| 6,344,475 | B1 | 2/2002 | Caplan |
| 6,576,273 | B2 | 6/2003 | Madsen |
| 6,592,896 | B2 | 7/2003 | Rosenbloom |
| 6,827,951 | B2 | 12/2004 | Newmark |
| 6,942,881 | B2 | 9/2005 | Madsen |
| 6,982,099 | B2 | 1/2006 | Newmark |
| 6,991,814 | B2 | 1/2006 | Ray |
| 7,037,524 | B2 | 5/2006 | Gow |
| 7,041,321 | B2 | 5/2006 | Newmark |
| 7,067,159 | B2 | 6/2006 | Newmark |
| 7,070,816 | B2 | 7/2006 | Newmark |
| 2002/0136786 | A1 | 9/2002 | Newmark |
| 2004/0247664 | A1 | 12/2004 | Dreja |
| 2005/0049299 | A1* | 3/2005 | Aggarwal ............... A61K 31/12 514/456 |
| 2005/0123632 | A1 | 6/2005 | Chen |
| 2006/0051438 | A1 | 3/2006 | Ray |

FOREIGN PATENT DOCUMENTS

| | | | |
|---|---|---|---|
| CN | 1515310 A * | 7/2004 | |
| CN | 1548121 A | 11/2004 | |
| EP | 1465646 A1 | 10/2004 | |
| IN | 457/RQ/CHE/2003 | 7/2005 | |
| IN | 200430 | 5/2006 | |
| JP | 2000-228966 A | 8/2000 | |
| JP | 2004524304 A | 8/2004 | |
| JP | 2004331539 A | 11/2004 | |
| WO | WO 2000/059523 A1 | 10/2000 | |
| WO | WO 2001/000201 A1 | 1/2001 | |
| WO | WO 2002/032444 A1 | 4/2002 | |
| WO | WO 02074295 A1 | 9/2002 | |
| WO | WO 03/049753 A1 | 6/2003 | |
| WO | WO 03/075685 A1 | 9/2003 | |

OTHER PUBLICATIONS

Jayaprakasha, GK, Jena, BS, Negi, PS, and Sakariah, KK, Evaluation of Antioxidant Activities and Antimutagenicity of Turmeric Oil: A Byproduct from Curcumin Production, Biosciences, 57(9/10):828-835 (2002).

Kelloff, GJ, Crowell, JA, Hawk ET, Steele, VE, Lubet, RA, Boone, CW, Covey JM, Doody, LA, Omenn, GS, Greenwald, P, Hong, WK, Parkinson, DR, Bagheri, D, Baxter, GT, Blunden, M, Doeltz, MK, Eisenhauer, KM, Johnson, K, Knapp, GG, Longfellow, DG, Malone, WF, Nayfield, SG, Seifried, HE, Swall, LM, and Sigman, CC, Strategy and Planning for Chemopreventive Drug Development: Clinical Development Plans II, Journal of Cellular Biochemistry, 26S: 54-71 (1996).

Rao, CV, Rivenson, A, Simi, B, and Reddy, BS, Chemoprevention of Colon Carcinogenesis by Dietary Curcumin, a Naturally Occuring Plant Phenolic Compound, Cancer Research, 55:259-266 (1995).

Subramanian, M, Sreejayan, Rao, MNA, Devasagayam, TPA, and Singh, BB, Diminution of Singlet Oxygen-Induced DNA Damage by Curcumin and Related Antioxidants, Mutation Research, 311:249-255 (1994).

Tennesen, HH, and Greenhill, JV, Studies on Curcumin and Curcuminoids, XXII: Curcumin as a Reducing Agent and as a Radical Scavenger, International Journal of Pharmaceutics, 87:79-87 (1992).

Reddy, ACP, and Lokesh, BR, Studies on the Inhibitory Effects of Curcumin and Eugenol on the Formation of Reactive Oxygen Species and the Oxidation of Ferrous Iron, Molecular and Cellular Biochemistry, 137:1-8 (1994).

Donatus, IA, Sardjoko, and Vermeulen, NPE, Cytotoxic and Cytoprotective Activities of Curcumin, Biochemical Pharmacology, 39(12):1869-1875 (1990).

Sharma, SC, Mukhtar, H, Sharma, SK, Murti, CRK, Lipid Peroxide Formation in Experimental Inflammation, Biochemical Pharmacology, 21:1210-1214 (1972).

Liu, J-Y, Lin, S-J, and Lin, J-K, Inhibitory Effects of Curcumin on Protein Kinase C Activity Induced by 12-O-tetradecanoyl-Phorbol-13-Acetate in NIH 3T3 Cells, Carcinogenesis, 14(5):857-861 (1993).

Huang, T-S, Lee, S-C, and Lin, J-K, Suppression of c-Jun/AP-1 Activation by an inhibitor of Tumor Promotion in Mouse Fibroblast Cells, Proc. Natl. Acad. Sci. U.S.A., 88:5292-5296 (1991).

Huang, M-T, Lysz, T, Ferraro, T, and Conney, AH, Inhibitory Effects of Curcumin on Tumor Promotion and Arachidonic Acid Metabolism in Mouse Epidermis, Cancer Chemoprevention, pp. 375-391 (1992), CRC Press, Inc.

Huang, M-T, Lysz, T, Ferraro, T, Abidi, TF, Laskin, JD, and Conney, AH, Inhibitory Effects of Curcumin on In Vitro Lipoxygenase and Cyclooxygenase Activities in Mouse Epidermis, Cancer Research, 51:813-819 (1991).

Plummer, SM, Holloway, KA, Manson, MM, Munks, RJL, Kaptein, A, Farrow, S, and Howells, L, Inhibition of Cyclo-Oxygenase 2 Expression in Colon Cells by the Chemopreventive Agent Curcumin Involves Inhibition of NF-KB Activation Via the NIK/IKK Signalling Complex, Oncogene, 18:6013-6020 (1999).

Funk, CD, Funk, LB, Kennedy, ME, Pong, AS, and Fitzgerald, GA, Human Platelet / Erythroleukemia Cell Prostaglandin G/H Synthase: cDNA Cloning, Expression, and Gene Chromosomal Assignment, FASEB Journal, 5:2304-2312 (1991).

Subbaramaiah, K, Telang, N, Ramonetti, JT, Araki, R, Devito, B, Weksler, BB, and Dannenberg, AJ, Transcription of Cyclooxygenase-2 Is Enhanced in Transformed Mammary Epithelial Cells, Cancer Research, 56:4424-4429 (1996).

Dubois, RN, Awad, J, Morrow, J, Roberts, LJ, and Bishop, PR, Regulation of Eicosanoid Production and Mitogenesis in Rat Intestinal Epithelial Cells by Transforming Growth Factor-α and Phorbol Ester, J. Clin. Invest., 93:493-498 (1994).

Kelley, DJ, Mestre, JR, Subbaramaiah, K, Sacks, PG, Schantz, SP, Tanabe, T, Inoue, H, Ramonetti, JT, and Dannenberg, AJ, Benzo[a]pyrene Up-Regulates Cyclooxygenase-2 Gene Expression in Oral Epithelial Cells, Carcinogenesis, 18(4):795-799 (1997).

Huang, M-T, Smart, RC, Wong, C-Q, and Conney, AH, Inhibitory Effect of Curcumin, Chlorogenic Acid, Caffeic Acid, and Ferulic Acid on Tumor Promotion in Mouse Skin by 12-O-Tetradecanoylphorbol-13-Acetate, Cancer Research, 48:5941-5946 (1988).

Asai, A and Miyazawa, T, Occurence of Orally Administered Curcuminoid as Glucuronide and Clucuronide/Sulfate Conjugates in Rat Plasma, Life Sciences, 67:2785-2793 (2000).

Ravindranath, V, and Chandrasekhara, N, In Vitro Studies on the Intestinal Absorption of Curcumin in Rats, Toxicology, 20:251-257 (1981).

Limtrakul, P, Lipigorngoson, S, Namwong, O, Apisariyakul, A, and Dunn, FW, Inhibitory Effect of Dietary Curcumin on Skin Carcinogenesis in Mice, Cancer Letters, 116:197-203 (1997).

Inano, H, and Onoda, M, Prevention of Radiation-Induced Mammary Tumors, Int. J. Radiation Oncology Biol. Phys., 52(1):212-223 (2002).

Inano, H, and Onoda, M, Radioprotective Action of Curcumin Extracted From Curcuma Longa Linn: Inhibitory Effect on Formation of Urinary 8-Hydroxy-2-Deoxyguanosine, Tumorigenesis, But

(56) References Cited

OTHER PUBLICATIONS

Not Mortality, Induced by γ-Ray Irradiation, Int. J. Radiation Oncology Biol. Phys., 53(3):735-743 (2002).
Shoba, G, Joy, D, Joseph, T, Majeed, M, Rajendran, R, and Srinivas, PSSR, Influence of Piperine on the Pharmacokinetics of Curcumin in Animals and Human Volunteers, Planta Medica, 64:353-356 (1998).
Began, G, Sudharshan, E, Sankar, KU, and Rao, AGA, Interaction of Curcumin With Phosphatidylcholine: A Spectrofluorometric Study, J. Agric. Food Chem, 47:4992-4997 (1999).
Lantz, RC, Chen, GJ, Solyom, AM, Jolad, SD, and Timmermann, BN, The Effect of Turmeric Extracts on Inflammatory Mediator Production, Phytomedicine 12:445-452 (2005).
Nishiyama, T, Mae, T, Kishida, H, Tsukagawa, M, Mimaki, Y, Kuroda, M, Sashida, Y, Takahashi, K, Kawada, T, Nakagawa, K, and Kitahara, M, Curcuminoids and Sesquiterpenoids in Turmeric (*Curcuma longa* L) Suppress an Increase in Blood Glucose Level in Type 2 Diabetic KK-A$^y$ mice, J. Agric. Food Chem, 53:959-963 (2005).
Li, L, Braiteh, FS, and Kurzrock, R, Liposome-Encapsulated Curcumin, In Vitro and In Vivo Effects on Proliferation, Apoptosis, Signaling, and Angiogenesis, Cancer, 104(6):1322-1331 (2005).
Kumar, V, Lewis, SA, Mutalik, S, Shenoy, DB, Venkatesh and Udupa, N, Biodegradable Microspheres of Curcumin for Treatment of Inflammation, Indian J Physical Pharmacol, 46(2): 209-217 (2002).
Ammon, HPT, and Wahl, MA, Pharmacology of Curcuma Longa, Planta Med, 57:1-7, (1991).
Ravindranath, V, and Chandrasekhara, N, Absorption and Tissue Distribution of Curcumin in Rats, Toxicology, 16: 259-265 (1980).
Wahlstrom, B and Blennow, G, A Study on the Fate of Curcumin in the Rat, Acta Pharmacol. et Toxicol., 43:86-92 (1978).
Monograph, *Curcuma longa* (Turmeric), Alternative Medicine Review, vol. 6 (Supplement): S62-S66 (2001).
Piyachaturawat, P, Glinsukon, T, and Toskulkao, C, Acute and Subacute Toxicity of Piperine in Mice, Rats and Hamsters, Toxicology Letters, 16:351-359 (1983).
Matsuo, T, Toyota, A, Kanamori, H, Nakamura, K, Katsuki, S, Sekita, S, and Satake, M, Constituents of Representative Curcuma and Estimation of *Curcuma* Species in Health Foods, Bulletin of the Hiroshima Prefectural Institute of Public Health and Environment, 10:7-13 (2002), Japan Science and Technology Agency. Abstract.
Kawamori, T, Lubet, R, Steele, VE, Kelloff, GJ, Kaskey, RB, Rao, CV, and Reddy, BS, Chemopreventive Effect of Curcumin, A Naturally Occuring Anti-Inflammatory Agent, During the Promotion/Progression Stages of Colon Cancer, Cancer Res., 59:597-601 (1999), American Association for Cancer Research.
Mahmoud, NN, Carothers, AM, Grunberger, D, Bilinski, RT, Churchill, MR, Martucci, C, Newmark, HL, and Bertagnolli, MM, Plant Phenolics Decrease Intestinal Tumors in an Animal Model of Familial Adenomatous Polyposis, Carcinogenesis, 21(5):921-927 (2000), Oxford University Press.
Zhang, F, Altorki, NK, Mestre, JR, Subbaramaiah, K, and Dannenberg, AJ, Curcumin Inhibits Cyclooxygenase-2 transcription in Bile Acid- and Phorbol Ester-Treated Human Gastrointestinal Epithelial Cells, Carcinogenesis, 20(3): 445-451 (1999), Oxford University Press.
Ireson, C, Orr, S, Jones, DJL, Verschoyle, R, Lim, C-K, Luo, J-L, Howells, L, Plummer, S, Jukes, R, Williams, M, Steward, WP, and Gescher, A, Characterization of Metabolites of the Chemopreventive Agent Curcumin in Human and Rat Hepatocytes and in the Rat in Vivo, and Evaluation of Their Ability to Inhibit Phorbol Ester-Induced Prostaglandin E$_2$ Production, Cancer Res., 61: 1058-1064 (2001), American Association for Cancer Research.
Sharma, RA, McLelland, HR, Hill, KA, Ireson CR, Euden, SA, Manson MM, Pirmohamed, M, Marnet, LJ, Gescher, AJ, and Steward, WP, Pharmacodynamic and Pharmacokinetic Study of Oral Curcuma Extract in Patients with Colorectal Cancer, Clin. Cancer Res., 7:1894-1900 (2001), American Association for Cancer Research.

Pan, M-H, Huang, T-M, and Lin, J-K, Biotransformation of Curcumin Through Reduction and Glucoronidation in Mice, Drug Metabolism and Disposition, 27(1):486-494 (1999), American Society for Pharmacology and Experimental Therapeutics.
Ireson, CR, Jones, DJL, Orr, S, Coughtrie, MWH, Boocock, DJ, Williams, ML, Farmer, PB, Steward, WP, and Gescher, AJ, Metabolism of the Cancer Chemopreventive Agent Curcumin in Human and Rat Intestine, Cancer Epidemiology, Biomarkers & Prevention, 11:105-111 (2002), American Association for Cancer Research.
Perkins, S, Verschoyle, RD, Hill, K, Parveen, I, Threadgill, MD, Sharma, RA, Williams, ML, Steward, WP, and Gescher, AJ, Chemopreventive Efficacy and Pharmacokinetics of Curcumin in the Min/+ Mouse, A Model of Familial Adenomatous Polyposis, Cancer Epidemiology, Biomarkers & Prevention, 11: 535-540 (2002), American Association for Cancer Research.
Chuang, SE, Kuo, ML, Hsu, CH, Chen, CR, Lin, JK, Lai, GM, Hsieh, CY, and Cheng, AL, Curcumin-Containing Diet Inhibits Diethylnitrosamine-Induced Murine Hepatocarcinogenesis, Carcinogenesis, 21(2):331-335 (2000), Oxford University Press.
Inano, H, Onoda, M, Inafuku, N, Kubota, M, Kamada, Y, Osawa, T, Kobayashi, H, and Wakabayashi, K, Potent Preventive Action of Curcumin on Radiation-Induced Initiation of Mammary Tumorigenesis in Rats, Carcinogenesis, 21(10): 1835-1841 (2000), Oxford University Press.
Garcea, G, Berry, DP, Jones, DJL, Singh, R, Dennison, AR, Farmer, PB, Sharma, RA, Steward, WP, and Gescher, AJ, Consumption of the Putative Chemopreventive Agent Curcumin by Cancer Patients: Assessment of Curcumin Levels in the Colorectum and their Pharmacodynamic Consequences, Cancer Epidemiology, Biomarkers & Prevention, 14(1) 120-125 (2005), American Association for Cancer Research.
Govindarajan, VS and Stahl, WH, Turmeric—Chemistry, technology, and Quality, CRC Critical Reviews in Food Science and Nutrition, 12(3):199-301 (1980).
Sharma RA, Ireson, CR, Verschoyle, RD, Hill, KA, Williams, ML, Leuratti, C, Manson, MM, Marnett, LJ, Steward, WP, and Gescher, A, Effects of Dietary Curcumin on Glutathione S-Transferase and Malondialdehyde-DNA Adducts in Rat Liver and Colon Mucosa: Relationship with Drug Levels, Clinical Cancer Research, 7:1452-1458 (2001).
Sharma, RA, Euden, SA, Platton, SL, Cooke, DN, Shafayat, A, Hewitt, HR, Marczylo, TH, Morgan, B, Hemigway, D, Plummer, SM, Pirmohamed, M, Gescher, AJ and Steward, WP, Phase I Clinical Trial of Oral Curcumin: Biomarkers of Systemic Activity and Compliance, Clinical Cancer Research, vol. 10, 6847-6854 (Oct. 15, 2004).
Hong CH, Kim Y, and Lee SK, Sesquiterpenoids from the Rhizome of Curcuma Zedoaria, Arch Pharm Res., 24(5): 424-426 (2001).
G. Scapagnini, R Foresti, V. Calabrese, AM Giuffrida Stella, CJ Green, and R. Motterlini, Caffeic Acid Phenethyl Ester and Curcumin: A Novel Class of Heme Oxygenase-1 Inducers, Molecular Pharmacology, 61(3):554-561 (2002).
Supplementary European Search Report (3 pages) dated Dec. 14, 2009.
Anna Carolina CM Manzan, Toniolo FS, Bredow E, and Povh, NP, Extraction of Essential Oil and Pigments from *Curcuma longa*[L.] by Steam Distillation and Extraction with Volatile Solvents, Journal of Agricultural and Food Chemistry, 51:6802 6807 (2003).
Negi PS, Jayaprakasha GK, Rao LJM, and Sarkaria KK, Antibacterial Activity of Turmeric Oil: A Byproduct from Curcumin Manufacture, J. Agric. Food Chem., 47:4297-4300 (1999).
Hong CH, Noh MS, Lee WY and Lee SK, Inhibitory Effects of Natural Sesquiterpenoids Isolated from the Rhizomes of Curcuma zedoaria on Prostaglandin E2 and Nitric Oxide Production, Planta Med, 68:545-547 (2002).
Craig WJ, The Golden Touch of Turmeric, Vibrant Life, 19 (3): 38-39 (2003), ProQuest Central.
Sandur SK, Pandey MK, Sung B, Ahn KS, Murakami A, Sethi G, Limtrakul P, Badmaev V and Aggarwal BB, Curcumin, Demethoxycurcumin, Bisdemethoxycurcumin, Tetrahydrocurcumin and Turmerones Differentially Regulate Anti-Inflammatory and Anti-Proliferative Responses Through a ROS-Independent Mecha-

(56) References Cited

OTHER PUBLICATIONS nism, Carcinogenesis Advance Access, originally published online on May 23, 2007, Carcinogenesis 28(8):1765-1773 (2007); doi:10.1093/carcin/bgm123.

Asche SL and Thakkar SK, Oil Extraction Increases Curcumin Availability from Turmeric Sources, FASEB Journal, 18 (4-5): Abstract 115.7 (2004).

Fujii Masami et al., Ingredient that improves bio-availability of curcumin, latest edition of Natural Food coloring material, Korin Publishing Co., Ltd., pp. 168-172 (2001).

Janaki, N and Bose, JL, An Improved Method for the Isolation of Curcumin From Turmeric, *Curcuma Longa*, L, Journal of Indian Chemical Society, 44 (11):985-986 (1967).

Krishnamurthy, N, Mathew, AG, Nambudiri, ES, Shivashankar, S, Lewis, YS, and Natarajan, CP, Oil and Oleoresin of Turmeric, Trop. Sci., 18(1):37-45 (1976).

Huang, M-T, Lou, Y-R, MA, W, Newmark, HL, Reuhl, KR and Conney, AH, Inhibitory Effects of Dietary Curcumin on Forestomach, Duodenal, and Colon Carcinogenis in Mice, Cancer Research, 54:5841-5847 (1994).

Pabon, HJJ, A Synthesis of Curcumin and Related Compounds, Recueil, 83:379-386 (1964).

Xu, Y, KU, B-S, Yao, H-Y, Lin, Y-H, Ma, X, Zhang, Y-H, Li, X-J, Antidepressant effects of curcumin in the forced swim test and olfactory bulbectomy models of depression in rats, Pharmacology Biochemistry and Behavior, 82(1): 200-206 (2005), Elsevier, Inc.

Yu, ZF, Kong, LD, and Chen, Y, Antidepressant activity of aqueous extracts of Curcuma longa in mice, Journal of Ethnopharmacology, 83(1-2): 161-165 (2002), Elsevier Science Ireland Ltd.

Funk, JL, Oyarzo, JN, Frye, JB, Chen, G, Lantz, RC, Jolad, SD, Solyom, AM, and Timmermann, BN, Turmeric extracts containing curcuminoids prevent experimental rheumatoid arthritis, Journal of Natural Products, 69(3): 351-355 (2006), American Chemical Society and American Society of Pharmacology.

Begum, AN, Jones, MR, Lim, GP, Morihara, T, Kim, P, Heath, DD, Rock, CL, Pruitt, MA, Yang, F, Hudspeth, B, Hu, S, Faull, KF, Teter, B, Cole, GM, and Frautschy, SA, Curcumin structure-function, bioavailability, and efficacy in models of neuroinflammation and Alzheimer's disease, Journal of Pharmacology and Experimental Therapeutics, 326(1): 196-208 (2008).

Zhang, L, Fiala, M, Cashman, J, Sayre, J, Espinosa, A, Mahanian, M, Zaghi, J, Badmaev, V, Graves, MC, Bernard, G and Rosenthal, M, Curcuminoids enhance amyloid-β uptake by macrophages of Alz,heimer's disease patients, Journal of Alzheimer's Disease, 10(1):1-7 (2006), IOS Press and the authors.

Eight (8) pages of Supplementary European Search Report dated Sep. 10, 2013 in Application No. EP 11765176.

Hashibe, M, Sankaranarayanan, R, Thomas,G, Kuruvilla, B, Mathew, B, Somanathan, T, Parkin, DM and Zhang, ZF, Alcohol drinking, body mass index and the risk of oral Leukoplakia in an Indian population, Int. J. Cancer, 88:129-134 (2000).

Kaur, J, Srivastava, A, and Ralhan, R, Over expression of p53 protein in betel- and tobacco-related human oral dysplasia and squamous cell carcinoma in India, Int. J. Cancer, 58(3):340-345 (1994).

Silverman, S, Bilimoria, KF, Bhargava, K, Mani, NJ, and Shah, RA, Cytologic, histologic and clinical correlations of precancerous and cancerous oral lesions in 57,518 industrial workers of Gujarat, India, Acta Cytol.,21 (2):196-198 (1977).

Silverman, S, Bhargava, K, Mani, NJ, Smith, LW, and Malaowalla, AM, Malignant Transformation and Natural History of Oral leukoplakia in 57,518 Industrial Workers of Gujarat, India, Cancer, 38:1790-1795 (1976).

Slaughter, DP, Southwick, HW, and Smejkal, W, Field Cancerization in oral stratified Squamous epithelium, Sixth Annual Cancer Symposium of the James Ewing Society, Cancer, 6:963-968 (1953).

Saleheen, D, Ali, SA, Ashfaq, K, Siddiqui, AA, Agha, A and Yasinzai, MM, Latent Activity of Curcumin against Leishmaniasis in Vitro, Biol. Pharm. Bull. 25(3) 386-389 (2002).

Koide, T, Nose, M, Ogihara, Y, Yoshisada, Y, and Ohta, N, Leishmanicidal Effect of Curcumin in Vitro, Biol. Pharm. Bull., 25(1):131-133 (2002).

Gomes, DCF, Alegrio, LV, Lima, MEF, Leon, LL, and Araujo, CAC, Synthetic derivatives of curcumin and their activity against Leishmania amazonensis, Arzneim-Forsch/Drug Res., 52(2):120-124 (2002).

Wu, NC, Safety and Anti-Inflammatory Activity of Curcumin: A Component of Tumeric (*Curcuma longa*), The Journal of Alternative and Complementary Medicine, 9(1):161-168 (2003).

Strong, MS, Incze, J., and Vaughan, CW, Field cancerization in the aerodigestive tract—its etiology, manifestation, and significance, J Otolaryngol, 13(1):1-6 (1984).

Pandey, M, Thomas, G, Somanathan, T, Sankaranarayanan, R, Abraham, E K., Jacob, B J, and Mathew, B, Evaluation of surgical excision of non-homogeneous oral leukoplakia in a screening intervention trial, Kerala, India, Oral Oncol., 37:103-109 (2001).

Antony, B, Benny, M, Rao, SB, Enhancing the Absorption of Curcuminoids, Spice India; Jul. 23-26, 2005.

Benny, M, Antony, B, Bioavailability of Biocurcumax™ (BCM-095™), Spice India; Nov. 15, 2006.

Antony, B, Merina, B, Iyer, VS, Judy, N, Lennertz, K, Joyal, S, A pilot cross-over study to evaluate human oral bioavailability of BCM-95® CG (Biocurcumax™), a novel bioenhanced preparation of curcumin, Indian journal of pharmaceutical sciences, 70(4):445(2008).

\* cited by examiner

FORMULATION OF CURCUMIN WITH ENHANCED BIOAVAILABILITY OF CURCUMIN AND METHOD OF PREPARATION AND TREATMENT THEREOF

This Application is a continuation of co-pending PCT Application Ser. No. PCT/IN2013/000673, filed Oct. 31, 2013, which claims priority from Indian Provisional application 4128/CHE/2012, filed Nov. 3, 2012, and a continuation-in-part of co-pending Ser. No. 14/206,044 filed Dec. 3, 2014, and is a continuation-in-part of co-pending U.S. application Ser. No. 14/476,555, filed Sep. 3, 2014, which is a divisional of co-pending U.S. application Ser. No. 13/645,031 filed Oct. 4, 2012, which is a continuation-in-part of PCT Application Serial No. PCT/IN2011/000232, filed Apr. 4, 2011, which claims priority of Indian Provisional Application Serial No. 950/CHE/2010, filed Apr. 5, 2010, and a continuation-in-part of co-pending U.S. application Ser. No. 14/520,292, filed Oct. 21, 2014, which is a divisional of Ser. No. 14/094,725, filed Dec. 2, 2013, which is a divisional of U.S. application Ser. No. 13/385,717, filed Mar. 5, 2012, which is a divisional of Ser. No. 12/926,985 filed Dec. 21, 2010, which is a divisional of Ser. No. 12/662,740 filed Apr. 30, 2010, which is a divisional of U.S. application Ser. No. 11/635,599 filed Dec. 8, 2006, which is a continuation of PCT Application Serial No. PCT/IN05/00176, filed May 30, 2005, and a continuation-in-part of co-pending U.S. application Ser. No. 14/623,608, filed Feb. 17, 2015, which is a divisional of Ser. No. 13/674,249, filed Nov. 12, 2012, which is a divisional of Ser. No. 13/506,572, filed Apr. 30, 2012, which is a divisional of Ser. No. 12/926,980, filed Dec. 21, 2010, which is a divisional of Ser. No. 12/073,864, filed Mar. 11, 2008, which is a continuation-in-part of Ser. No. 11/635,599, filed Dec. 8, 2006, which is a continuation of PCT Application Serial No. PCT/IN05/00176, filed May 30, 2005, and a continuation-in-part of co-pending U.S. application Ser. No. 14/206,044, filed Mar. 12, 2014, which is a continuation-in-part of U.S. Appl. Ser. No. 13/645031 filed Oct. 4, 2012, Ser. No. 13/674,249 filed Nov. 12, 2012, 14/094/725 filed Dec. 2, 2013, and claims the benefit of 61/794,175 filed Mar. 3, 2015, all of which applications are incorporated in entirety by reference.

OBJECTIVES

The disclosure relates to a formulation of curcuminoid with essential oil of turmeric to enhance the bioavailability of curcumin and to augment the biological activity of curcumin, wherein curcumin is the main constituent of curcuminoid and wherein Ar-turmerone is the main constituent of the essential oil of turmeric. Such enhanced bioavailability of curcumin has been demonstrated in human volunteers. The disclosure provides a method of treatment of several conditions and diseases by orally administering a blend of curcuminoids and essential oil of turmeric. The disclosure provides a method of oral supplementation of a composition having curcuminoids and essential oil of turmeric for the treatment of head and neck cancer premalignant lesions.

BACKGROUND

Curcumin [1,7-bis(4-hydroxy-3-methoxyphenyl)-1,6-heptadiene-3,5-dione]

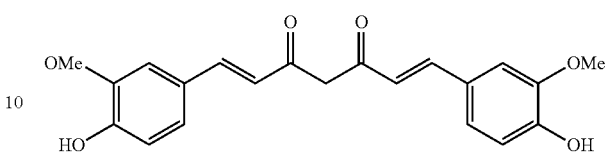

is the major yellow pigment of turmeric, a commonly used spice, derived from the rhizome of the herb *Curcuma longa* Linn. In the Indian subcontinent and Southeast Asia, turmeric has traditionally been used as a treatment for inflammation, skin wounds, and tumors. Clinical activity of curcumin is yet to be confirmed; however, in preclinical animal models, curcumin has shown cancer chemo preventive, antineoplastic and anti-inflammatory properties (Kelloff, G. I., et al, J. Cell Biochem., 1996, 265:54-71). Especially interesting is its ability to prevent the formation of carcinogen-induced intestinal premalignant lesions and malignancies in rat (Rao, C. V. et al, Cancer Res., 1995, 55:259-66. Kawamori, T. et al, Cancer Res., 1999, 59:597-601) and in the multiple neoplasia (Min/+) mouse (Mahmood, N. N. et al, Carcinogenesis, 2000, 31:921-27), a genetic model of the human disease familial adenomatous polyposis. Curcumin acts as a scavenger of oxygen species such as hydroxyl radical, superoxide anion and singlet oxygen (Subramanian, M. et al, Mutat. Res., 1994, 311:249-55; Tonnesen, H. H. et al, Int. J. Pharm., 1992, 87:79-87; Reddy, A. C. P. et al, Mol. Cell Biochem, 1994, 137:1-8) and interferes with lipid peroxidation (Donatus, I. A., Biochem. Pharmacol., 1990, 39:1869-75; Sharma, S. C. et al, Biochem. Pharmacol., 1972, 21:1210-14). Curcumin suppresses a number of key elements in cellular signal induction pathways pertinent to growth, differentiation and malignant transformations. Among signaling events inhibited by curcumin are protein kinases (Liu, J. V. et al, Carcinogenesis, 1993, 14:857-61), c-Jun/AP-1 activation (Huang, T. S. et al, Proc. Natl. Acad. Sci., 1991, 88:5292-96), prostaglandin biosynthesis (Huang, M-T. et al, In L. W. Battenberg (ed.) Cancer Chemo prevention, CRC Press, Boca Raton, 1992, pp 375-91) and activity and expression of the enzyme cyclooxygenase-2 (Huang, M. T., et al, Cancer Res., 1991, 51:813-19; Zhang, F. et al, Carcinogenesis, 1999, 20:445-51). This latter property is probably mediated by the ability of curcumin to block activation of the transcription factor NF-κB at the level of the NF-κB inducing kinase/IKKα/β signalling complex (Plummer, S. et al, Oncogene, 1999, 18:6013-20).

Curcumin directly inhibits cyclooxygenase-2 and also inhibits the transcription of the gene responsible for its production. Cyclooxygenases (COX) catalyze the synthesis of prostaglandins (PGs) from arachidonic acid. There are two isoforms of COX, designated COX-1 and COX-2. COX-1 is expressed constitutively in most tissues and appears to be responsible for housekeeping functions (Funk, C. D. et al, FASEB J., 1991, 5:2304-12) while COX-2 is not detectable in most normal tissues but is induced by oncogenes, growth factors, carcinogens and tumor promoters (Subbaramiah, K. et al, 1996, Cancer Res., 1996, 56:4424-29; DuBois, R. N. et al, J. Clin. Invest., 1994, 93:493-98; Kelley, D. J. et al, Carcinogenesis, 1997, 18:795-99). Several different mechanisms account for the link between COX-2 activity and carcinogenesis.

Curcumin is not simply an alternative to non-steroidal anti-inflammatory drugs (NSAIDS), which also have anti-inflammatory and cancer chemopreventive properties. This is so because COX is a bifunctional enzyme with cyclooxygenase and peroxidase activities. Aside from being important for PG synthesis, the peroxidase function contributes to the activation of procarcinogens. Therefore, the failure of NSAIDS to inhibit the peroxidase function of COX potentially limits their effectiveness as anticancer agents. Curcumin, in contrast, down-regulates levels of COX-2 and thereby decreases both the cyclooxygenase and peroxidase activities of the enzyme.

Curcumin is among the few agents to block both the COX and LOX (lipoxygenase) pathways of inflammation and carcinogenesis by directly modulating arachidonic acid metabolism. In a study to evaluate the effect of curcumin on the metabolism and action of arachidonic acid in mouse epidermis, it was found that topical application of curcumin inhibited arachidonic acid-induced ear inflammation in mice (Huang, M. T., et al Cancer Res., 1988, 48:5941-46; 1991, 51:813-19). Curcumin (10 µM) inhibited the conversion of arachidonic acid to 5- and 8-hydroxyeicosatetraenoic acid by 60% and 51%, respectively (LOX pathway) and the metabolism to PGE2, PGF2α and PGD2 by 70%, 64% and 73%, respectively (COX pathway). In another study, dietary administration of 0.2% curcumin to rats inhibited azoxymethane-induced colon carcinogenesis and decreased colonic and tumor phospholipase A2, phospholipase Cγl, and PGE2 levels (Rao, C. V. et al., Cancer Res., 1995, 55:259-66). In this study, dietary curcumin also decreased enzyme activity in the colonic mucosa and tumors for the formation of PGE2, PGF2α, PGD2, 6-keto-PGF2α and thromboxane B2 via the COX system and production of 5(S)-, 8(S)-, 12(S)-, and 15(S)-hydroxy-eicosatetraenoic acid via the LOX pathway was also inhibited.

Despite this impressive array of beneficial bioactivities, the bioavailability of curcumin in animals and man remains low. In rodents, curcumin demonstrates poor systemic bioavailability after p.o. dosing (Ireson, C. R. et al, Cancer Res., 2001, 41:1058-64) which may be related to its inadequate absorption and fast metabolism. Curcumin bioavailability may also be poor in humans as seen from the results of a recent pilot study of a standardized turmeric extract in colorectal cancer patients (Sharma, R. A. et al, Clin. Cancer Res., 2001, 7:1834-1900). Indirect evidence suggests that curcumin is metabolized in the intestinal tract. Curcumin undergoes metabolic O-conjugation to curcumin glucuronide and curcumin sulfate and bioreduction to tetrahydrocurcumin, hexahydrocurcumin and hexahydrocurcuminol in rats and mice in vivo (Pan, M. H. et al, Drug Metabol. Dispos., 1999, 27:486-94; Asai, A., et al, Life Sci., 2000, 67:2785-93) in suspensions of human and rat hepatocytes (Ireson et al, loc. cit) and in human and rat intestine (Ireson, C. R. et al, Cancer Epidemiol. Biomark. Prev., 2002, 11:105-11). Metabolic conjugation and reduction of curcumin was more in human than in rat intestinal tissue. It has been suggested that the intestinal tract plays an important role in the metabolic disposition of curcumin. This is based predominantly on experiments in which [$^3$H] labeled curcumin was incubated with inverted rat gut sacs (Ravindranath, V. and Chandrasekhara, N., Toxicology, 1981, 20:251-57). This was later confirmed in intestinal fractions from humans and rats. Intestinal mucosa, as well as liver and kidney tissue from the rat, can glucurodinate and sulfate curcumin, as judged by the analysis of differential amounts of curcumin present before and after treatment of tissue extracts with conjugate-hydrolyzing enzymes (Asai et al, loc cit). Thus, gut metabolism contributes substantially to the overall metabolic yield generated from curcumin in vivo. In human intestinal fractions, conjugation with activated sulfuric or glucuronic acids was much more abundant, whereas conjugation in human hepatic tissues was less extensive, than in the rat tissues (Ireson, C. R., et al, Cancer Epidemiol. Biomark. Prev., 2002, 11:105-11).

Although p.o. administered curcumin has poor bioavailability and only low or non-measurable blood levels were observed (Perkins, S. et al, Cancer Epidemiol. Biomark. Prev., 2002, 11:535-40), this route of administration inhibits chemically induced skin and liver carcinogenesis (Limtrakul, P., et al, Cancer Lett., 1997, 116:197-203; Chiang, S. E. et al, Carcinogenesis, 2000, 21:331-35). Oral administration of curcumin also inhibits the initiation of radiation-induced mammary and pituitary tumors (Inano, H. et al, Carcinogenesis, 2000, 21:1835-41; Int. J. Radiat. Oncol. Biol. Phys., 2002, 52:212-23; ibid, 2002, 53:735-43). Similarly, in a study to assess the curcumin levels in the colorectum, a daily dose of 3.6 g curcumin achieves pharmacologically effective levels in the colorectum with negligible distribution of curcumin outside the gut (Garcea, G. et al, Cancer Epidemiol. Biomark. Prev., 2005, 14:120-25).

Earlier Shobha et al (Shobha et al, Planta Med., 1998, 64:353-56) had observed that administering piperine along with curcumin enhances the bioavailability of curcumin. However, the level of enhancement was only modest and no curcumin could be detected after 3 hours even when supplemented with piperine.

Although some questions remain unanswered regarding the pharmacokinetics of curcumin in humans, there is no denying the fact that considerable proportion of ingested curcumin is excreted through feces and at least about one-half of absorbed curcumin is metabolized. The quantity of curcumin that reaches tissues outside the gut is probably pharmacologically insignificant. Several studies have failed to demonstrate the positive invitro results with curcumin in invivo animal and human studies due to lack of absorption of curcumin after oral administration. To provide the clinical benefits, curcumin must be absorbed from its oral route of administration at a suitable rate, be distributed in adequate concentration in the blood and remain in the system for a sufficient period at an effective concentration level.

Both turmeric and curcumin are known for their antioxidant and anti-inflammatory activities, and may play roles in preventing atherosclerosis and cancer. Pharmacologically, turmeric has also been found to be a stimulant, a tonic, a carminative, and an anti-helmintic (Saleheen D, A. S. A., Ashfaq K, Siddiqui A A, Agha A, Yasinzai M M, Latent activity of Curcumin and their activity against Leishmaniasis in vitro. Biol Pharm Bull, 2002. 25: p. 386-9; Koide T, N. M., Ogihara Y, Yabu Y, Ohta N, Leishmanicidal effect of curcumin in vitro. Biol Pharm Bull, 2002. 25: p. 131-3; Gomes Dde C, A. L. V., deLIMA M E, LEON 11 and Araujo C A, Synthetic derivatives of curcumin and their activity against Leishmania amazonensis. Arzneimittelforschung, 2002. 52: p. 120-4). Curcumin has antibacterial and anti-fungal, anti-inflammatory, anti-allergic and wound healing properties (N, C.-W., Safety and anti-inflammatory activity of curcumin: a component of tumeric (*Curcuma longa*). J Altern Complement Med., 2003. 9(1): p. 161-8).

A large proportion of head and neck cancer develop from pre-existing oral premalignant lesions. Through several strategies have been attempted to treat these premalignant lesions, none so far has been found to be fruitful. This includes surgical excision, which has a relapse rate of about 40% and various chemopreventive agents. These are retinoid (vitamin-A), beta-carotine, Ketorolac (anti-inflammatory agent) and cetuximab (anti-EGFR therapy). Most of these agents although has demonstrated initial response, the lesions often relapsed upon cessation of the therapy. In addition, these treatments had various degrees of toxicities.

Head and neck squamous cell carcinoma (HNSCC) is the sixth most common cancer in the world and leading cancer in India. The age standardized incidence (ASR) range from 6.5 per 100,000 in Bangalore to 15.9 per 100,000 in the state of Kerala. While HNSCC account for 3% of all new cancer cases and 2% of cancer deaths in the United States in 1999, in India, it accounts for 30% of all cancers. Similarly, the incidence of oral leukoplakia in this population is also high. Case-control and cohort studies have established that this high incidence is due to widespread habit of tobacco use and alcohol exposure (Hashibe, M., Sankaranarayanan, R, Thomas, G, Kuruvilla, B, Mathew, B, Somanathan, T, Parkin D M, Zhang, Z F, Alcohol drinking, body mass index and the risk of oral leukoplakia in an Indian population. Int J Cancer, 2000. 88(1): p. 129-34). Tobacco is mostly consumed as smokeless tobacco in the form of pan. The incidence of p53 expression in premalignant lesion was reported as 55% (15/27) and that in the oral squamous cell carcinoma as 75% (24/32), where as normal epithelium did not show positive p53 expression (0/24) (Kaur J. et al, Overexpression of p53 protein in betel and tobacco related human oral dysplasia and squamous-cell carcinoma in India. Int. J. Cancer., 1994. 58(3): p. 340-5).

The malignant transformation rate of oral premalignant lesions from is about 8-36%, reported to be similar to that in other parts of the world (Gupta P C, Leukoplakia and incidence of oral cancer. J Oral Pathol, 1989. 18(1): p. 17). In a landmark primary prevention study of oral cancer (Gupta P C, et al., Intervention study for primary prevention of oral cancer among 36000 Indian tobacco users. Lancet, 1986. 1(8492): p. 1235-9) 36,471 subjects from Kerala, Andhra Pradesh and Gujarat were followed for 5 years. The follow up rate was 97%. Smoke cessation program was introduced in the interventional group. 5-year age adjusted incidence rate (per 100,000) of leukoplakia was 11.4 in the interventional group versus 47.8 among men and 5.8 versus 33.0 among women.

Silverman and his coworkers (Silverman Sol. Bilimoria K F. Bhargava K. Mani N J. Shah R A, Cytologic, histologic and clinical correlations of precancerous and cancerous oral lesions in 57,518 industrial workers of Gujarat, India. Acta Cytologica., 1977. 21(2): p. 196-8) screened a group of 57,518 industrial workers in India for oral cancer and pre cancer lesions. Fifty-one oral cancers were diagnosed (0.18%). In a follow up study of the same cohort identified 6,718 subjects with oral leukoplakia. After 2 years 4762 (71%) were reexamined Six (0.13%) individuals with leukoplakia developed oral cancer. This incidence of malignant transformation (63/100,000 per year), was similar to that reported from the US population. During the two year follow up period 57.3% lesions remained unchanged, 31.6% disappeared, and 11% had altered appearance (Silverman S. Bhargava K. Smith L W. Malaowalla A M. Malignant transformation and natural history of oral leukoplakia in 57, i.w.o.G., India., Malignant transformation and natural history of oral leukoplakia in 57,518 industrial workers of Gujarat, India. Cancer, Boone J Cell Biochem Suppl, 1976, 1992. 38(4): p. 1790-5, 23-6)

Within the upper aero digestive tract mucosa of patients at risk for tobacco related cancers, a well-defined precursor oral premalignant lesion (OPL) for oral and pharyngeal carcinoma has been defined, i.e. oral mucosal dysplasia (Pindborg J J, Oral Cancer and Precancer. Bristol: John Wright and Sons, 1980; Lippman, S. M. and W. K. Hong, Molecular markers of the risk of oral cancer. N Engl J Med, 2001. 344(17): p. 1323-6). Clinically these dysplastic lesions appear as white (leukoplakia) and red (erythroplakia) patches or as mixed (speckled leukoplakia) lesions. These lesions have variable malignant transformation potential. Oral and pharyngeal mucosa lesions transform into invasive tumors through well defined histological stages of hyperplasia, dysplasia, carcinoma in situ and invasive squamous cell carcinoma. The genetic changes associated with the histopathologic progression to upper aerodigestive squamous cell carcinoma has also has been established and a genetic carcinogenesis model has been proposed including early loss of heterozygosity (LOH) for tumor suppressor genes and later activation of protooncogenes (Slaughter D L, Southwick H W, and Smejkal W, "Field Cancerization" in oral stratified squamous epithelium: clinical implications of multicentric origin. Cancer Causes Control, 1953. 6: p. 963-8).

Prospective studies of subjects with OPLs revealed a significant incidence of malignant transformation to cancer depending primarily upon the presence of dysplasia. In the largest U.S. series consisting of 257 untreated oral leukoplakia subjects, Silverman et al., determined the malignant transformation rate at 8 years was 17.5%, however, the rate rose to 36.4% for those with dysplasia. None of the dysplastic lesions improved spontaneously. A large study by Silverman of Indian workers with OPL showed similar findings (Silverman Sol. Bilimoria K F. Bhargava K. Mani N J. Shah R A, Cytologic, histologic and clinical correlations of precancerous and cancerous oral lesions in 57,518 industrial workers of Gujarat, India. Acta Cytologica., 1977. 21(2): p. 196-8).

HNSCC results from a multi-step carcinogenesis process, which occurs over large areas of the upper aerodigestive tract epithelium exposed to carcinogens. This condemned mucosa contains multiple transformed clones that can develop into new primary tumors at a rate of 30% over five years. This process is called "field cancerization" (Strong M S, I. J., Vaughan C W, Field cancerization in the aerodigestive tract—its etiology, manifestation, and significance. J Otolaryngol, 1984. 13(1): p. 1-6; Pandey, M., Thomas, G., Somanathan, T., Sankaranarayanan, R., Abraham, E. K., Jacob, B. J., and Mathew, B., Evaluation of surgical excision of non-homogeneous oral leukoplakia in a screening intervention trial, Kerala, India. Oral Oncol, 2001. 37: p. 103-9). These patients harbor multifocal, metachronous, premalignant lesions. Currently there are no effective means of treating these lesions. Excision often leads to relapse. Although chemoprevention with retinoids has demonstrated proof-of-principle that this may be a potential approach to prevent oral cancer, the poor compliance and toxicity profile made this an ineffective.

The standard of care for OPLs is observation or removal. If the area is extensively involved, or multiplicity prohibits excision, the only alternative is close observation. The recurrence rate after excision of leukoplakia is 35% (P, N. P., Oral Oncol, 1997; Pandey, M., Thomas, G., Somanathan, T., Sankaranarayanan, R., Abraham, E. K., Jacob, B. J., and Mathew, B., Evaluation of surgical excision of non-homogeneous oral leukoplakia in a screening intervention trial, Kerala, India. Oral Oncol, 2001. 37: p. 103-9). Repeated surgical excisions can be associated with scarring and poor functional outcome.

Chemoprevention potential of several drugs has been investigated in the past with limited success. Following description summarize the outcome of these clinical trials.

Despite many clinical trials with retinoids, the narrow therapeutic window of these agents does not allow their safe routine use for these lesions (Lippman, S. M., Benner, S. E., and Hong, W. K., Cancer chemoprevention. J Clin Oncol, 1994. 12: p. 851-73).

A randomized, placebo-controlled, double blind trial evaluated the efficacy of 13-cis-retinoic acid in halting or reversing the development of OPLs. A total of 46 subjects were randomized to treatment with 13-cRA (1-2 mg/kg/day) or placebo for three months, with six further months of follow-up. Intolerable conjunctivitis and hypertriglyceridemia developed in 2 subjects receiving 2 mg/kg. Among the 24 13-cRA subjects, 2 had complete responses, 14 had partial responses, however, relapse occurred 2-3 months after end of 13-cRA therapy.

Another randomized, double-blind trial was designed to evaluate low-dose 13-cRA versus β-carotene in maintaining remission of oral premalignancy following induction therapy with high-dose 13-cRA. At the conclusion of induction, the rate of response was 55% (36 subjects), and the rate of stable disease was 35% (30 subjects). Of the 59 subjects included in the second phase, 53 were evaluable, of these, 22 in the 13-cRA group and 13 in the β-carotene group responded to maintenance therapy or continued to have stable lesions (92% vs. 45%).

A bio chemoprevention study employing a combination of 13-cRA, alpha-tocopherol and alpha-interferon was designed to address advanced premalignant lesions of the upper aerodigestive tract that are resistant to single agent retinoid intervention. At 6 months, 31 subjects were evaluable for response: 12 had a pathologic complete response, 7 partial response, and at 12 months, 8 complete and 7 partial responses.

Sulindac, a pan COX inhibitor is being tested for efficacy in the management of oral leukoplakia in a clinical trial at Amrita Institute of Medical Sciences (AIMS), Cochin. Sulindac has been shown to have anti-neoplastic effect against human oral squamous cell carcinoma in pre-clinical experiments. In addition, sulindac has been reported to be effective in preventing colon and esophagus tumors in several animal models. Recently, sulindac was shown to be safe and effective in humans for the prevention of polyps in familial adenomatous polyposis.

These studies were initiated because of the known dramatic over expression of Cyclooxygenase-2 (COX-2) in head and neck cancers and leukoplakia compared to normal tissue, and the known high levels of prostaglandins that may contribute to carcinogenesis in these patients.

The National Cancer Institute recently reported in the 2003 ASCO proceedings a negative trial of the topical NSAID Ketorolac for oral leukoplakia. The design of the proposed curcumin trial may allow efficacy not seen in the Ketorolac trial because of several differences. Curcumin is given systemically which might provide better drug distribution or availability, possible COX independent effects of these metabolites may lead to efficacy not apparent in the Ketorolac study.

Although the curcumin from turmeric can have wide medicinal use and biological effects have been suspected for over many decades, the challenge so far has been to increase bioavailability of the drug in blood, so that there will be tangible patient benefit.

SUMMARY

Disclosure relates to a medicinal composition useful for the treatment of head and neck cancer premalignant lesions comprising of curcuminoid mixture and added essential oil of turmeric. In some embodiments, the weight ratio of the curcuminoid mixture to the added essential oil of turmeric ranges from about 1:3 to about 99:1. In some other embodiments, the curcuminoid mixture includes curcumin, demethoxycurcumin and bisdemethoxycurcumin. In yet another embodiment, the essential oil of turmeric includes ar-turmerone. According to another embodiment, the essential oil of turmeric includes about 40-50% ar-turmerone.

Some embodiments provide a method of treating head and neck cancer premalignant lesions by administering a composition having a curcuminoid mixture and added essential oil of turmeric.

BRIEF DESCRIPTION OF THE DRAWINGS

The above objectives and advantages of the disclosed teachings will become more apparent by describing in detail preferred embodiments thereof with reference to the attached drawings in which.

DETAILED DESCRIPTION

Figure 1:
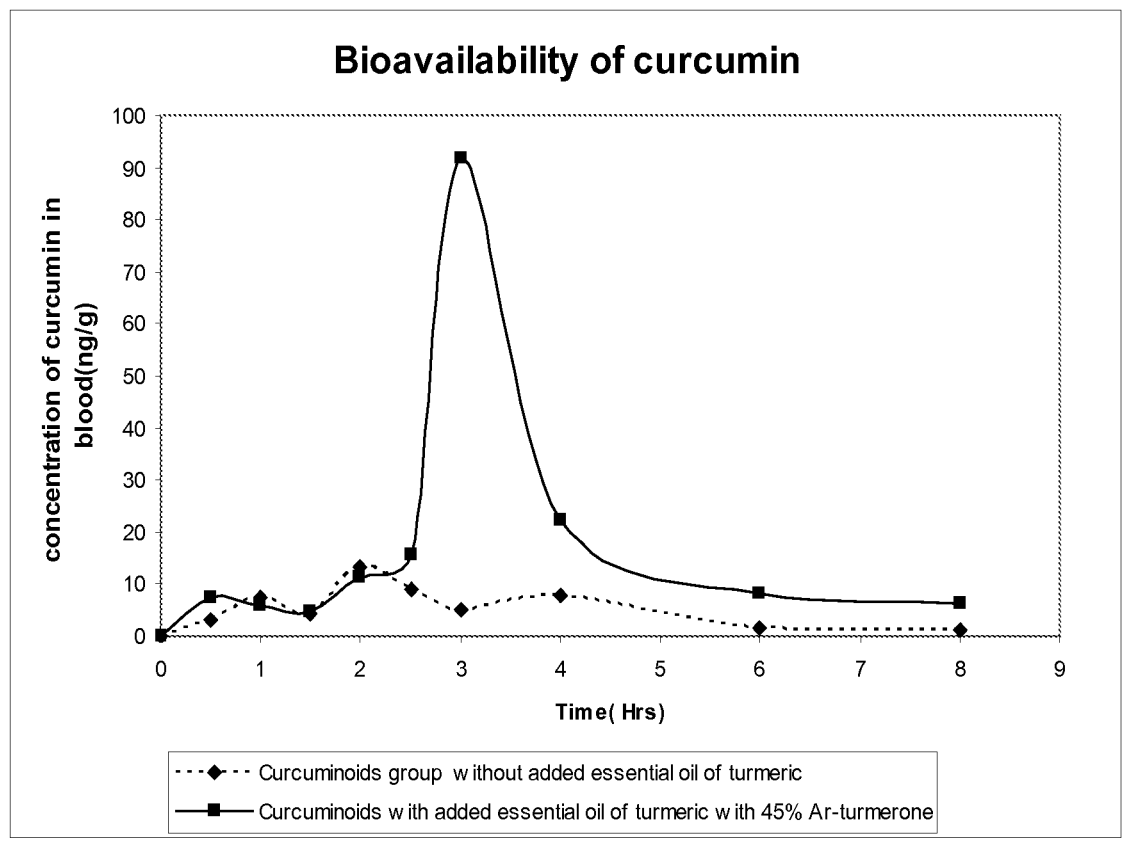
FIG. 1 provides a graph showing the bioavailability of curcumin in humans upon administration of (1) gelatin capsules, which were prepared by admixing curcuminoid isolated from turmeric with essential oil of turmeric, and, (2) gelatin capsules of curcuminoid alone, which were prepared without adding essential oil of turmeric to the curcuminoid isolated from turmeric. The x-axis shows time in hours following administration of the gelatin capsules. The y-axis shows the concentration of curcumin (ng/g) in blood.

The disclosure relates to a product to enhance the bioavailability of curcumin by mixing a suitable portion of the volatile oil obtained from turmeric with the curcuminoids isolated from turmeric.

As disclosed herein the term "curcuminoid" or "curcuminoid mixture" is a mixture of curcumin, demethoxycurcumin and bisdemethoxycurcumin.

In some embodiments, curcumin is the major component of the curcuminoid mixture. In some embodiments, demethoxycurcumin is a minor component of the curcuminoid mixture. In some embodiments bisdemethoxycurcumin is a minor component of the curcuminoid mixture. In some embodiments, 95% of the crystals having curcuminoid mixture are composed of curcumin, demethoxycurcumin and bisdemethoxycurcumin.

The term "essential oil" or "essential oil of turmeric" is also referred to as "volatile oil" or "volatile oil of turmeric." The essential oil of turmeric is a mixture of oils. Essential oil is obtained as a by-product during the extraction of curcumin or curcuminoids from turmeric.

In some embodiments, Ar-turmerone is the main constituent of essential oil. In some embodiments, ar-turmerone constitutes about 40-50% of the essential oil of turmeric. In some embodiments, Ar-turmerone constitutes about 45% of the essential oil of turmeric.

As stated herein, the term "a" or "an" refers to one or more.

As stated herein, the terms "isolated" and "purified" are referred to interchangeably.

The volatile oil of turmeric was isolated by conventional methods of steam distillation to isolate essential oils and is well known in the art.

Curcuminoid is isolated from the de-oiled turmeric by solvent extraction. Suitable solvents for this purpose include acetone, hexane, ethyl acetate, dicholoroethane, chloroform, etc. The extraction is conveniently carried out at moderate temperatures (40-55° C.) and the solvent is partially removed to yield a concentrate containing 30-60% solids. This solution is cooled to obtain crystals of curcuminoid which are isolated by any suitable method such as filtration or centrifugation. Analysis of this product, which is composed of the isolated crystals of curcumioid mixture, showed that, in some embodiments, 95% of the product was composed of curcumin, demethoxycurcumin and bisdemethoxycurcumin.

The disclosure provides a composition having curcuminoid and an essential oil of turmeric.

Curcuminoids and the volatile oils of curcumin are mixed and blended to get a uniform product. If small percentages (~5%) of the essential oil of turmeric are added to the curcuminoid, then the bioavailability of curcumin is significantly enhanced. Accordingly, a composition of curcuminoid admixed with a suitable proportion of Ar-turmerone (the main component of the turmeric essential oil) is provided.

Some embodiments provide a composition for enhanced bioavailability of curcumin. The composition includes a curcuminoid mixture and essential oil of turmeric. The curcuminoid mixture includes curcumin, demethoxycurcumin and bisdemethoxycurcumin. The essential oil of turmeric ranges from about 20% ar-turmerone to about 60% ar-turmerone. The weight ratio of the curcuminoid mixture to essential oil of turmeric ranges from about 1:3 to about 99:1.

In some embodiments, the weight ratio of the curcuminoid to the essential oil of turmeric ranges from about 1:1 to about 90:1. In some embodiments, the weight ratio of the curcuminoid to the essential oil of turmeric ranges from about 1:1 to about 3:1. The weight ratio of the curcuminoid to the essential oil of turmeric can be varied from about 3:1 to about 99:1. In some embodiments, the weight ratio of the curcuminoid to the essential oil of turmeric ranges from about 1:1 to about 70:1. In some embodiments, the weight ratio of the curcuminoid to the essential oil of turmeric ranges from about 1:1 to about 45:1. In some embodiments, the weight ratio of the curcuminoid to the essential oil of turmeric ranges from about 3:1 to about 50:1. In some embodiments, the weight ratio of the curcuminoid to the essential oil of turmeric ranges from about 8:1 to about 25:1. In some embodiments, the weight ratio of the curcuminoid to the essential oil of turmeric is about 90:7. In some embodiments, the weight ratio of the curcuminoid to the essential oil of turmeric is about 90:8. In some embodiments, the weight ratio of the curcuminoid to the essential oil of turmeric is about 90:9. In some embodiments, the weight ratio of the curcuminoid to the essential oil of turmeric is about 89:9. In some embodiments, the weight ratio of the curcuminoid to the essential oil of turmeric is about 89:8. In one embodiment, the ratio is about 85:15. In another embodiment, the ratio is about 92:8. In another embodiment, the ratio is about 95:5. In another embodiment the weight ratio is about 10:1. In some embodiments, the weight ratio is about 12:1. In some embodiments, the weight ratio of the curcuminoid to the essential oil of turmeric is about 1:2. In some embodiments, the weight ratio of the curcuminoid to the essential oil of turmeric is about 2:1. In some embodiments, the weight ratio of the curcuminoid to the essential oil of turmeric ranges from about 1:3 to about 99:1.

In some embodiments of the composition having curcuminoid and added essential oil of turmeric, the curcuminoid ranges, by weight, from about 24% to about 96%. In some embodiments of the composition having curcuminoid and added essential oil of turmeric, the curcuminoid ranges, by weight, from about 30% to about 96%. In some embodiments of the composition of curcuminoid and added essential oil of turmeric, the curcuminoid ranges, by weight, from about 40% to about 75%. In some embodiments of the composition having curcuminoid and added essential oil of turmeric, the curcuminoid ranges, by weight, from about 50% to about 60%.

In some embodiments of the composition having curcuminoid and added essential oil of turmeric, the demethoxycurcumin ranges, by weight, from about 5% to about 25%. In some embodiments of the composition having curcuminoid and added essential oil of turmeric, the demethoxycurcumin ranges, by weight, from about 10% to about 20%.

In some embodiments of the enhanced curcumin bioavailability composition having curcuminoid and added essential oil of turmeric, the bisdemethoxycurcumin ranges, by weight, from about 2% to about 7%.

In some embodiments of the enhanced curcumin bioavailability composition having curcuminoid and added essential oil of turmeric, the essential oil of turmeric ranges, by weight, from about 4% to about 50%. In some embodiments, of the composition of curcuminoid and added essential oil having turmeric, the essential oil of turmeric ranges, by weight, from about 15% to about 50%. In some embodiments of the composition having curcuminoid and added essential oil of turmeric, the essential oil of turmeric ranges, by weight, from about 20% to about 50%. In some embodiments of the composition having curcuminoid and added essential oil of turmeric, the essential oil of turmeric ranges, by weight, from about 25% to about 40%.

Some embodiments include a composition having a curcuminoid and an added amount of essential oil of turmeric, wherein the essential oil is present in an amount sufficient to cause an enhancement of bioavailability of the curcumin when administered to a human as compared to the bioavailability of curcumin upon administration of a composition prepared using curcuminoid alone without adding essential oil. Curcumin levels in blood samples is greater following administration of a composition having curcuminoid and added essential oil of turmeric as compared to a composition of curcuminoid alone. In some embodiments, the enhancement of bioavailability of curcumin following administration of a composition of curcuminoid and added essential oil of turmeric ranges from about 5-fold to about 16-fold. Enhancement of bioavailability of curcumin from a composition prepared by mixing curcuminoid and essential oil of turmeric is provided in FIG. 1 and Example 1.

In some embodiments, a composition of a curcuminoid and added essential oil of turmeric is orally administered to a human.

A method of extraction of curcuminoids includes treating dried and powdered rhizomes of turmeric with a solvent, followed by solvent stripping, and steam distilling to obtain an essential-oil free extract. The essential oil-free extract is cooled to about 4° C. to allow the curcuminoids to crystallize. The curcuminoids are then separated by filtration, centrifugation or any other method of solid-liquid separation well-known in the art. In some embodiments, 95% of the separated crystals are composed of curcumin, demethoxycurcumin and bisdemethoxycurcumin.

Curcuminoid is isolated from the de-oiled turmeric by solvent extraction. Suitable solvents for this purpose include acetone, hexane, ethyl acetate, dicholoroethane, chloroform, etc. The extraction is conveniently carried out at moderate temperatures (about 40° C. to about 55° C.) and the solvent is partially removed to yield a concentrate containing 30-60% solids. This solution is cooled to obtain crystals having curcuminoid mixture which are isolated by any suitable method such as filtration or centrifugation. 95% of this product (crystals) was composed of the curcuminoid mixture. The remaining may contain traces of essential oil plus other constituents such as carbohydrates, etc, which were not characterized.

The disclosure provides a method of extracting a curcuminoid from turmeric including:
drying rhizomes of turmeric to form a dried turmeric;
powdering the dried turmeric to form a powdered turmeric;
treating the powdered turmeric with a solvent selected from the group consisting of ethyl acetate, acetone, hexane, ethylene dichloride, ethyl alcohol, and combinations thereof to form a solution;
stripping the solvent from the solution to form an extract;
cooling the extract to about 4° C. to form crystals and a liquid, wherein the liquid includes the essential oil of turmeric and a resin; and
separating the crystals from the liquid to obtain the curcuminoid crystals.

In some embodiments, curcumin, demethoxycurcumin and bisdemethoxycurcumin comprise 95% of the curcuminoid crystals.

Some embodiments include a method of extracting a curcuminoid from turmeric by drying rhizomes of turmeric to form dried turmeric. The dried turmeric is powdered to form powdered turmeric. The powdered turmeric is treated with a solvent selected from the group consisting of ethyl acetate, acetone, hexane, and combinations thereof to form a solution. The solvent is stripped from the solution to form an extract. The extract is cooled to about 4° C. to form crystals having curcuminoid mixture, and, a liquid. The liquid includes the essential oil of turmeric and a resin. The crystals having the curcuminoid mixture are separated from the liquid. In some embodiments, 95% of the crystals having the curcuminoid mixture are composed of the curcuminoid mixture, namely, curcumin, demethoxycurcumin and bisdemethoxycurcumin.

The volatile oil of turmeric was isolated by conventional methods of steam distillation to isolate essential oils and is well known in the art.

Curcuminoid and the essential oil are blended in a suitable proportion by a process including, suspending the curcuminoid mixture in about 3 to 5 times its quantity of water, mixing in the essential oil, pulverizing in a colloidal mill into fine slurry, and stripping the slurry off water under heat and vacuum to obtain a uniform blend. Five hundred milligram capsules are made from this blend for human consumption.

The disclosure provides a method of preparing a composition including a curcuminoid mixture and an essential oil of turmeric including:
suspending the curcuminoid mixture in water to form a suspension;
adding the essential oil to the suspension to form a mixture;
homogenizing the mixture to obtain a fine slurry; and
drying the fine slurry under heat and vacuum to form a uniform blend of a composition including the curcuminoid and the essential oil of turmeric. Drying of the fine slurry under heat and vacuum can be performed using a vaccumized desolventiser with a stirrer.

A composition of curcuminoid and added essential oil of turmeric can be prepared by suspending the curcuminoid mixture in water to form a suspension. Essential oil is added to the suspension to form a mixture. The mixture is homogenized to form fine slurry. The fine slurry is dried under heat and vacuum to form a uniform blend of a composition of curcuminoid and an essential oil of turmeric. The fine slurry can be dried under heat and vacuum using, for example, a vaccumized desolventiser having a stirrer.

In one embodiment, a homogeneous mixture of curcuminoid and water is prepared by suspending the curcuminoid mixture in water to form a suspension. The suspension is homogenized to obtain fine slurry. The fine slurry is dried under heat and vacuum to form a composition having a homogeneous mixture of the curcuminoid and water.

The disclosure provides a method of preparing a homogeneous mixture having a curcuminoid and water by,
suspending a curcuminoid mixture in water to form a suspension;
homogenizing the suspension to obtain a fine slurry; and
drying the suspension under heat and vacuum to form a composition including a homogeneous mixture of the curcuminoid and water.

Hard gelatin capsules, which contain about 500 mg of a blend of curcuminoid and essential oil of turmeric, are prepared. A 500 mg capsule for enhanced bioavailability of curcumin, having the curcuminoid mixture and essential oil of turmeric in a weight ratio of about 95:5 is expected to contain about 460 mg of curcuminoid and about 40 mg of essential oil. The curcuminoid mixture is composed of curcumin, demethoxycurcumin and bisdemethoxycurcumin. In terms of active constituents, the respective figures would be about 437 mg of curcumin and about 18 mg of Ar-turmerone. In some embodiments, the gelatin capsules have about 300 mg to about 460 mg of curcuminoid and about 40 mg to about 375 mg of essential oil of turmeric. In some embodiments of the composition having curcuminoid and added essential oil of turmeric, wherein the gelatin capsule includes 500 mg of a blend of the curcuminoid and the essential oil. The curcuminoid in the blend ranges from about 300 mg to about 485 mg. The Ar-turmerone in the blend ranges from about 5 mg to about 200 mg.

Gelatin capsules with curcuminoid alone but without added essential oil were similarly prepared to study the comparative efficacies of the capsule containing added essential oil versus the capsule prepared without adding essential oil.

The disclosure provides a method of preparing a gelatin capsule having a curcuminoid and an essential oil of turmeric by suspending a curcuminoid mixture in water to form a suspension. Then adding an essential oil to the suspension to form a mixture. Then homogenizing the mixture to obtain a fine slurry. Then drying the slurry under heat and vacuum to form a uniform blend of a composition having the curcuminoid and the essential oil of turmeric. Then compressing the blend into the hard gelatin capsule.

Hard gelatin capsules of a composition having a curcuminoid and an added essential oil of turmeric can be prepared by compressing a uniform blend of the composition into a capsule. Gelatin capsules are prepared by standard methods using instrument such as a capsule filling machine manufactured by Pam Pharmaceuticals, Mumbai, India.

Another embodiment provides for an application of a formulation of curcuminoid with essential oil of turmeric with 45% Ar-turmerone for treating head and neck cancer premalignant lesions. Patients with head and neck cancer premalignant lesions were given capsules with curcuminoid with essential oil of turmeric with 45% Ar-turmerone in 10:1 and 12:1 ratio. The patients on curcuminoids with essential oil of turmeric with 45% Ar-t in 10:1 and 12:1 ratio formulation can lead to suppression of NF-kB, one of the central molecule involved in oral carcinogenesis, and COX2 in tissue, leading to reversal of the oral premalignant lesions and the response is durable.

The inventive compositions have the additional benefit that the essential oil components are themselves bioactive (for example, see Yue, A et al, Int. J. Mol. Med., 2002, 9:481-84; Jayaprakasha, G. K. et al, Z. Naturforsch., 2002, 57:828-35) and thus are expected to synergistically enhance the bioactivity of curcumin.

For the first time, we demonstrate that a composition having curcuminoids and essential oil of turmeric can increase bioavailability. The composition can suppress NF-kB mediated carcinogenesis in human. The composition can effectively treat head and neck cancer premalignant lesions. It was also demonstrated that this effect is durable. We demonstrate that curcuminoids when combined with turmeric essential oil allow sufficient quality of the drug to reach the systemic circulation and that can have durable anti-cancer effect.

We have demonstrated that the composition having curcuminoids and essential oil of turmeric when given as oral tablets (1500 mg/day for six months) in patients with oral premalignant lesions can lead to regression of the oral premalignant lesions. Follow up of these patients for six months after cessation of medication has demonstrated that the response is durable. We have also demonstrated that administration of oral curcuminoids with essential oil of turmeric can lead to suppression of NF-kB one of the central molecules involved in oral carcinogenesis. These are the findings of a human study of 40 patients with oral premalignant lesions treated by the combination of curcuminoids with essential oil of turmeric. The medication was well tolerated with no evidence of local or systemic toxicities.

The disclosed compositions can be administered to a human for treating conditions including various human cancers such as colon cancer, colorectal cancer, prostate cancer, breast cancer, lung cancer, oral cancer, liver cancer, uterine, cervical cancer, renal cancer, skin cancer, gastric cancer, pancreatic cancer, tumours and leukemias, etc It will be readily understood by the skilled artisan that numerous alterations may be made to the examples and instructions given herein. These and other objects and features will be made apparent from the following examples. The following examples as described are not intended to be construed as limiting the scope of the subject matter.

EXAMPLES

Example 1

Nine healthy human volunteers aged between 25 and 45 years of age were selected for the study. They were given capsules of curcuminoid mixture alone and capsules of enhanced curcumin capsules at the dosage of 50 mg curcuminoid/kg body weight. Enhanced curcumin is a composition having curcuminoid and added essential oil of turmeric. In the enhanced curcumin capsules the weight ratio of curcuminoid to essential oil of turmeric was 10:1. The subjects were advised to take curcuminoid capsules first. Blood samples were collected at zero hour and periodically at one-hour or half-hour intervals for 8 hours. After a washout period of one week, the same protocol was repeated with enhanced curcumin bioavailability capsules. The whole blood was extracted exhaustively with ethyl acetate to recover curcumin. The ethyl acetate extract was analyzed by HPLC on a RP-C18 column (25×4 5 mm) using tetrahydrofuran (THF) as solvent and UV detection at 420 nm. The eluant flow rate was 1 ml/min. Efficiency of the extraction procedure for recovering curcumin from blood samples was determined by measuring recovery of curcumin upon extraction of normal blood samples. Normal blood samples were collected by adding curcumin to normal blood (of persons not consuming curcumin or enhanced curcumin capsules). Curcumin was extracted from the normal blood samples by the above procedure. The efficiency of recovery of curcumin by the above extraction procedure was estimated to range between 80.12% and 86.49%. A typical result is given in Table 1.

TABLE 1

| | Curcumin content in blood (ng/g) | |
|---|---|---|
| Time (h) | Curcumin composition | Enhanced curcumin bioavailability composition |
| 0.0 | 0.0 | 0 |
| 0.5 | 3.17 | 7.85 |
| 1.0 | 7.57 | 6.23 |
| 1.5 | 4.42 | 4.84 |

TABLE 1-continued

| | Curcumin content in blood (ng/g) | |
|---|---|---|
| Time (h) | Curcumin composition | Enhanced curcumin bioavailability composition |
| 2.0 | 13.81 | 11.95 |
| 2.5 | 9.61 | 19.22 |
| 3.0 | 5.67 | 92.59 |
| 4.0 | 8.2 | 24.33 |
| 6.0 | 1.62 | 8.43 |
| 8.0 | 1.11 | 5.09 |

The results were also graphically represented in FIG. 1. Following administration of capsules having a 10:1 weight ratio of curcuminoid to essential oil of turmeric, the peak absorption of curcumin occurred at 3 hr. Furthermore, curcumin persisted in small amounts in the blood till 8 hr beyond which measurements were not made. At peak absorption the enhancement of bioavailability ranged, among the 9 persons, between 5 and 16-fold with a mean value of 10.62.

Example 2

Human subjects were administered capsule (4×500 mg) prepared with curcuminoids and without added essential oil of turmeric (curcuminoids group in Table 2). Blood was drawn at different intervals (one hour) and tested for curcumin content. After two weeks the same groups were administered an enhanced curcumin bioavailability composition (4×500 mg). The varying ratios of curcuminoids and added essential oil of turmeric were as provided in Table 2. Blood from the enhanced curcumin group was drawn at different intervals and tested for curcumin content. As seen in Table 2, bioavailability of curcumin was greater when enhanced curcumin capsules were administered as compared to administration of capsule containing curcuminoids without added essential oil of turmeric.

TABLE 2

Curcumin content in blood (AUC) after administration of curcuminoid mixture alone and enhanced curcumin bioavailability composition.

| | Curcumin content in blood (AUC) | |
|---|---|---|
| Ratio of curcuminoids to added essential oil of turmeric | Curcuminoid mixture alone group | Enhanced curcumin bioavailability composition |
| 90:4 | 725 | 5147.5 |
| 90:5 | 820 | 5904 |
| 90:6 | 750 | 5475 |
| 90:7 | 900 | 6300.0 |
| 90:8 | 752 | 5367.6 |
| 90:9 | 782 | 5552.2 |
| 89.9 | 696 | 5080.8 |
| 90:10 | 760 | 5320 |
| 80:9 | 726 | 5227.2 |
| 80:20 | 754 | 5315.7 |
| 90:20 | 765 | 5469.75 |
| 70:20 | 810 | 5147.5 |

The ratios of curcuminoids to added essential oil of turmeric in the enhanced curcumin bioavailability compositions provided in Table 2 can also be represented as shown in Table 3. The unit of curcumin content in blood was provided as area under the curve (AUC).

TABLE 3

Ratio of curcuminoids to added essential oil in compositions for enhanced curcumin bioavailability.

| Ratio of Curcuminoids to added essential oil of turmeric | Ratio of curcuminoids to added essential oil of turmeric |
|---|---|
| 90:4 | 22.5:1 |
| 90:5 | 18:1 |
| 90:6 | 15:1 |
| 90:7 | 12.8:1 |
| 90:8 | 11.25:1 |
| 90:9 | 10:1 |
| 90:10 | 9:1 |
| 80:9 | 8.9:1 |
| 80:20 | 4:1 |
| 90:20 | 4.5:1 |
| 70:20 | 3.5:1 |

Example 3

Bioavailability of Curcumin from Essential Oil of Turmeric Alone, Raw Turmeric Powder, Curcuminoid Alone, Curcuminoid with Essential Oil of Turmeric with 45% Ar-turmerone in 10:1 Ratio and Curcuminoid with Essential Oil of Turmeric with 45% Ar-turmerone in 12:1 Ratio Etc.

Nine healthy human volunteers were given capsules containing 475 mg of curcuminoid mixture without added essential oil of turmeric (the capsule was made up to 500 mg by addition of rice powder) at a dosage of 50 mg curcuminoid/kg body weight. Blood was drawn from the subjects at baseline, 0.5, 1, 1.5, 2, 2.5, 3, 4, 6 and 8 hours post drug. The same subjects after a washout period of one week were given 500 mg capsule having 454.55 mg curcuminoid mixture with 45.45 mg essential oil of turmeric, wherein the essential oil of turmeric had about 45% Ar-turmerone (the weight ratio of curcuminoid mixture to added essential oil of turmeric was 10:1) at a dosage of 50 mg curcuminoid/kg body weight of the subject. Blood was drawn from the subjects at baseline, 0.5, 1, 1.5, 2, 2.5, 3, 4, 6 and 8 hours post drug. Table 4 provides the amount of curcumin in nanograms per gram of blood for the subjects, which was averaged for each time point.

The above protocol was repeated with the following four formulations:

A capsule having 500 mg of essential oil of turmeric, wherein the essential oil of turmeric had 10-15% Ar-turmerone, was administered at a dosage of 50 mg of essential oil of turmeric per kg body weight of the human subject;

A capsule having 500 mg of essential oil of turmeric, wherein the essential oil of turmeric had 45% Ar-turmerone, administered at a dosage of 50 mg of essential oil of turmeric per kg body weight of the human subject; and A capsule having 500 mg of raw turmeric powder was administered at a dosage of 50 mg of raw turmeric powder/kg body weight of the human subject. A capsule having 500 mg of 461.5 mg curcuminoid mixture with 38.45 mg essential oil of turmeric, wherein the essential oil of turmeric had about 45% Ar-turmerone (the weight ratio of curcuminoid mixture to added essential oil of turmeric was 12:1)

Whole blood drawn from the subjects was extracted exhaustively with ethyl acetate to recover curcumin. The ethyl acetate extract was analyzed by HPLC on a RP-C18 column (25×4 5 mm) using tetrahydrofuran (THF) as solvent and UV detection at 420 nm. The eluent flow rate was 1 ml/min. As seen in Table 4 and FIG. 2, curcumin bioavailability in human subjects following administration of raw turmeric was low. Curcumin bioavailability following administration of essential oil fractions having 10-15% or 45% Ar-turmerone was not detectable (referred to as Nd in Table 4). Whereas, curcumin was detectable in human subjects following administration of curcuminoid mixture without added essential oil of turmeric, the bioavailability of curcumin was enhanced by about 6.7 fold upon administration of a composition having curcuminoid mixture and essential oil of turmeric with 45% Ar-t in 10:1 ratio and the bioavailability of curcumin was enhanced by about 8.3 fold upon administration of a composition having curcuminoid mixture and essential oil of turmeric with 45% Ar-t in 12:1 ratio.

Figure 2:
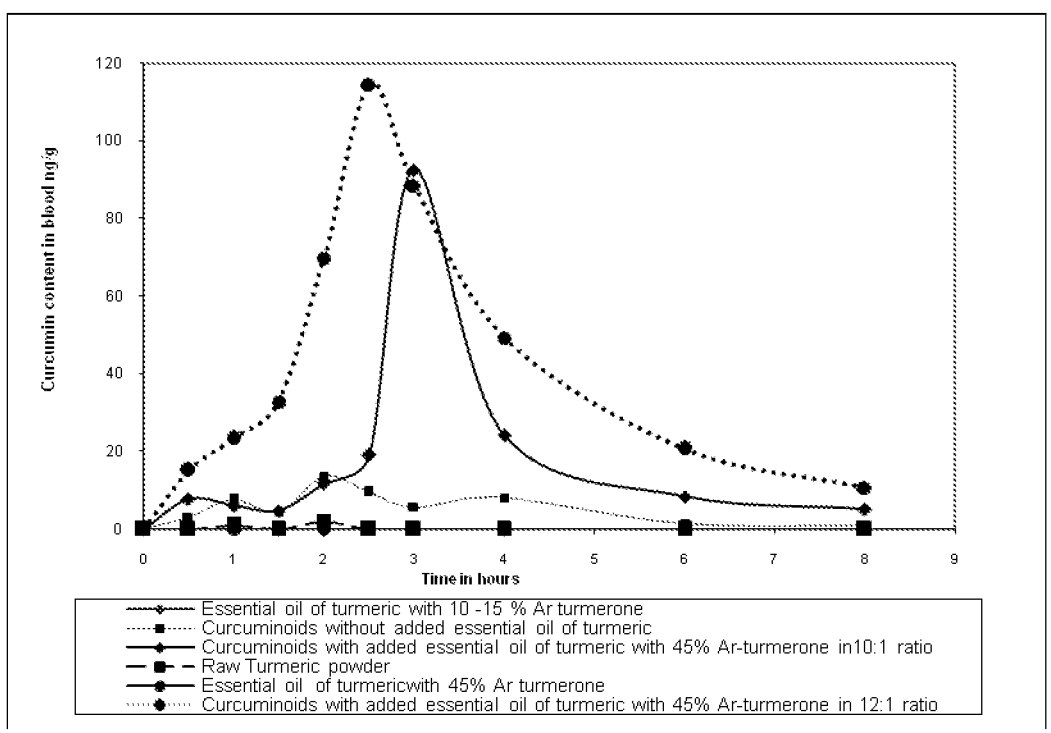
FIG. 2 provides a graph showing the bioavailability of curcumin in human upon administration of 1) gelatin capsule, which were prepared by admixing curcuminoid with added essential oil of turmeric with 45% Ar-turmerone in 10:1 ratio, 2) gelatin capsules of curcuminoid alone, which were prepared without adding essential oil of turmeric to the curcuminoid isolated from turmeric, 3) gelatin capsules of raw turmeric powder alone, 4) gelatin capsules of Essential oil of turmeric with 45% Ar-turmerone alone, 5) gelatin capsules of essential oil of turmeric with 10-15% Ar-turmerone alone. 6) gelatin capsule, which were prepared by admixing curcuminoid with added essential oil of turmeric with 45% Ar-turmerone in 12:1 ratio, The x-axis shows time in hours and y-axis shows the concentration of curcumin (ng/g) in blood.

As seen in FIG. 2, the maximum concentration of curcumin in blood (Cmax of curcumin) was 13.81 ng/g upon administration of the negative control capsule having curcuminoid mixture without the added essential oil of turmeric, whereas, the Cmax of curcumin was 92.59 ng/g upon administration of the positive control capsule having curcuminoid mixture and added essential oil of turmeric with 45% Ar-t in 10:1 ratio. The Cmax of curcumin was 114.59 ng/g upon administration of the positive control capsule having curcuminoid mixture and added essential oil of turmeric with 45% Ar-t in 12:1 ratio. Therefore, comparison of the Cmax values shows that bioavailability of curcumin upon oral administration of the claimed composition having curcuminoid mixture and added essential oil of turmeric with 45% Ar-t in 10:1 was about 6.7 times greater than bioavailability of curcumin upon oral administration of curcuminoid mixture without the added essential oil of turmeric. Bioavailability of curcumin upon oral administration of the claimed composition having curcuminoid mixture and added essential oil of turmeric with 45% Ar-t in 12:1 ratio was 8.3 times greater than bioavailability of curcumin upon oral administration of curcuminoid mixture without the added essential oil of turmeric.

Human volunteers aged between 25 and 45 years were randomized into separate groups having 3 subjects each (Groups A through W). For control experiment, at the initial time point, subjects in all the groups were four 500 mg capsules of curcuminoid mixture without added essential oil of turmeric (referred to as C without added E) having about 475 mg of curcuminoid mixture. Then blood was drawn from the subjects at different time periods (0.5, 1, 1.5, 2, 2.5, 3, 4, 6 and 8 hours post drug) and the amount of curcumin in blood (in nanograms per gram of blood) was determined. The average values of curcumin in blood at each time period was plotted in separate graphs for each of the groups (A to W). For each of the groups, the area under the curve (AUC) of curcumin was calculated from the figure. In Table 5 and FIG. 3, AUC was provided as nanograms of curcumin per gram of blood.

After a wash out period of 2 weeks, subjects in groups A through W were given four 500 mg capsules each, wherein set of 4 capsules had varying ratios of curcuminoid mixture to added essential oil of turmeric (referred to as C with added E capsule in Table 5), and wherein the essential oil of turmeric in the capsules had 45% Ar-turmerone. The ratio of curcuminoid mixture to essential oil of turmeric in the capsules ranged from about 99:1 to about 1:3. Some of the could be expressed as more than one type of ratio, for example, as 95:5 or 19:1; 90:4 or 22.5:1; 90:5 or 18:1; 90:6 or 15:1; 90:7 or 12.8:1; 90:8 or 11.3:1; 90:9 or 10:1; 90:10 or 9:1; 90:20 or 4.5:1; 89:9 or 9.8:1; 80:9 or 8.8:1; 80:20 or 4:1; 70:20 or 3.5:1; 75:25 or 3:1; 60:30 or 2:1; 50:50 or 1:1, 30:60 or 1:2 and 25:75 or 1:3 and therefore the ratios were referred to accordingly in Table 5.

As shown in Table 5, each of the groups was administered a capsule having a different weight ratio of curcuminoid

TABLE 4

Comparison of curcumin bioavailability from raw turmeric powder, essential oil of turmeric with 45% Ar-turmerone, essential oil of turmeric with 10-15% Ar-turmerone, curcuminoid mixture alone, curcuminoid mixture with added essential oil of turmeric with 45% Ar-turmerone in 10:1, curcuminoid mixture with added essential oil of turmeric with 45% Ar-urmerone in 12:1.

Curcumin content in blood (ng/g)

| Time in hours | Raw turmeric powder | Essential oil of turmeric (45% Ar-turmerone) | Essential oil of turmeric (10-15% Ar-turmerone) | Curcuminoid mixture without added Essential oil of turmeric | Curcuminoid mixture with added essential oil of turmeric (45% Ar-turmerone) 10:1 | Curcuminoid mixture with added essential oil of turmeric (45% Ar-turmerone) 12:1 |
|---|---|---|---|---|---|---|
| 0 | 0 | 0 | 0 | 0 | 0 | 0 |
| 0.5 | Nd | Nd | Nd | 3.17 | 7.85 | 15.2 |
| 1 | 1.05 | Nd | Nd | 7.57 | 6.23 | 23.4 |
| 1.5 | Nd | Nd | Nd | 4.42 | 4.84 | 32.8 |
| 2 | 2.1 | Nd | Nd | 13.81 | 11.95 | 69.8 |
| 2.5 | Nd | Nd | Nd | 9.61 | 19.22 | 114.59 |
| 3 | Nd | Nd | Nd | 5.67 | 92.59 | 88.5 |
| 4 | Nd | Nd | Nd | 8.2 | 24.33 | 49.4 |
| 6 | Nd | Nd | Nd | 1.62 | 8.43 | 20.74 |
| 8 | Nd | Nd | Nd | 1.11 | 5.09 | 10.8 |

Example 4

Bioavailability of Curcumin from Capsules Having Weight Ratio of Curcuminoid Mixture to Essential Oil of Turmeric Ranging from about 1:3 to 99:1 mixture to essential oil of turmeric (referred to as C:E). Blood was drawn from the subjects and the AUC was calculated as described above. The curcumin content in the blood for each group was expressed as AUC, which was used to compare the bioavailability of curcumin from the different treatment groups.

Figure 3:
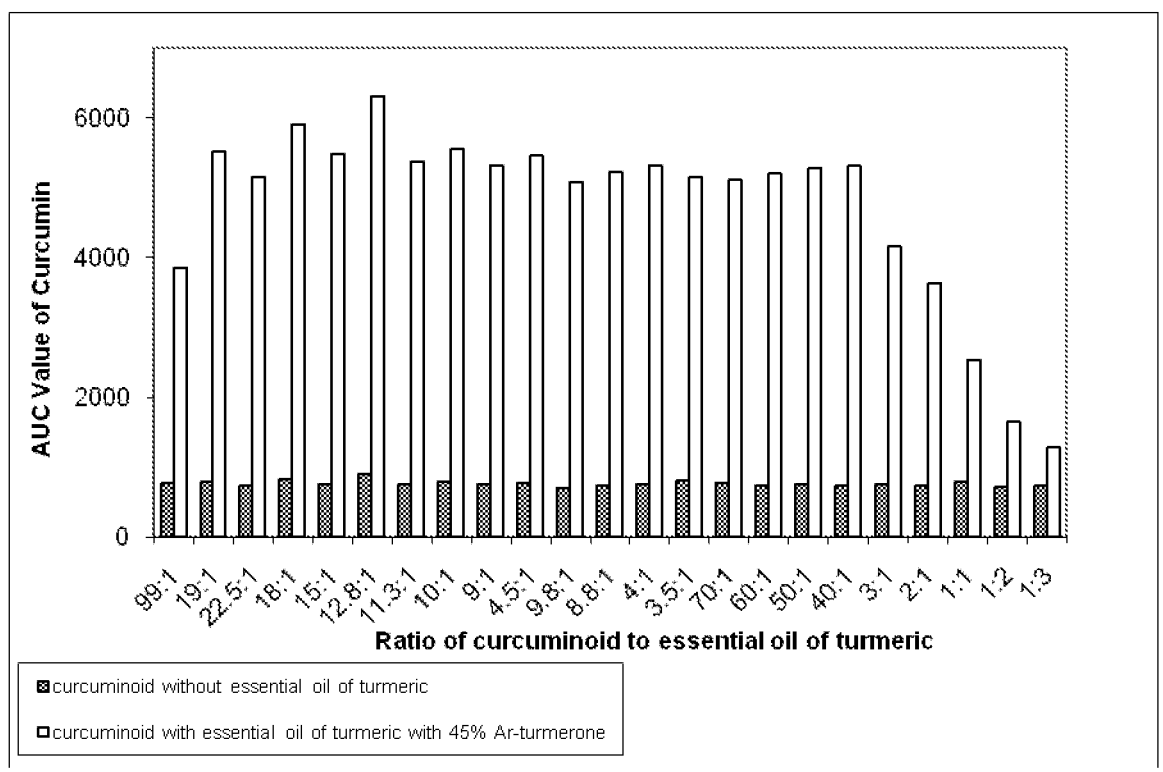
FIG. 3 provides a comparison of the bioavailability of curcumin from the curcuminoid mixture without added essential oil of turmeric group and the curcuminoid mixture with added essential oil of turmeric with 45% Ar-turmerone in a weight ratio ranging from about 1:3 to 99:1. The x-axis shows the ratio of curcumin to essential oil of turmeric and y-axis shows the AUC value of curcumin.

Table 5 and FIG. 3 provide a comparison of the bioavailability of curcumin from the curcuminoid mixture without added essential oil of turmeric as the control group and the curcuminoid mixture with added essential oil of turmeric with 45% Ar-turmerone.

As seen in Table 5 and FIG. 3, curcumin bioavailability upon administration of capsules having curcuminoid mixture with added essential oil of turmeric with 45% Ar-turmerone resulted in an enhancement of bioavailability ranging from 1.8 to 7.3 fold over the curcumin bioavailability that was observed when negative control capsules having curcuminoid mixture without added essential oil of turmeric were administered. The results in Table 5 further show that the enhancement of bioavailability was observed over the entire claimed range of the ratio about 1:3 to about 99:1 of curcuminoid mixture to essential oil of turmeric.

component such as curcuminoid mixture or essential oil or the combination of curcuminoid mixture and essential oil, then the capsules were made up to 500 mg by addition of a placebo, e.g, rice powder. In one treatment, each capsule had a 1:10 ratio of curcuminoid mixture to added essential oil of turmeric. Each capsule contained 20 mg curcuminoid and 200 mg essential oil of turmeric, wherein the essential oil of turmeric had 10 to 15% Ar-turmerone (referred to as Ar-t in Table 6).

In another treatment, each capsule had a 1:10 ratio of curcuminoid mixture to added essential oil of turmeric, wherein the essential oil had 45% Ar-turmerone. Each capsule contained 20 mg curcuminoid and 200 mg essential oil of turmeric. The capsule was referred to as 20 mg C: 200 mg E=1:10 (E had 10-15% Ar-t) in Table 6.

TABLE 5

Bioavailability of curcumin from compositions having weight ratios of curcuminoid mixture to added essential oil of turmeric ranging from 1:3 to 99:1

| Group | Ratio of C:E | Dosage 4 caps each | C without added E | | C with added E | | |
|---|---|---|---|---|---|---|---|
| | | | C (mg) per capsule | C (ng) per gm of blood (AUC) | C (mg) per capsule | E (mg) per capsule | C (ng) per gm of blood (AUC) |
| A | 99:1 | 500 mg | 475 | 771 | 495 | 5 | 3855 |
| B | 95:5 or 19:1 | 500 mg | 475 | 786 | 475 | 25 | 5515 |
| C | 90:4 or 22.5:1 | 500 mg | 475 | 725 | 478.72 | 21.28 | 5147.5 |
| D | 90:5 or 18:1 | 500 mg | 475 | 820 | 473.68 | 26.32 | 5904 |
| E | 90:6 or 15:1 | 500 mg | 475 | 750 | 468.75 | 31.25 | 5475 |
| F | 90:7 or 12.8:1 | 500 mg | 475 | 900 | 463.77 | 36.23 | 6300 |
| G | 90:8 or 11.3:1 | 500 mg | 475 | 752 | 459.35 | 40.65 | 5367.6 |
| H | 90:9 or 10:1 | 500 mg | 475 | 782 | 454.55 | 45.45 | 5552.2 |
| I | 90:10 or 9:1 | 500 mg | 475 | 760 | 450 | 50 | 5320 |
| J | 90:20 or 4.5:1 | 500 mg | 475 | 765 | 409.1 | 90.9 | 5469.75 |
| K | 89:9 or 9.8:1 | 500 mg | 475 | 696 | 453.7 | 46.3 | 5080.8 |
| L | 80:9 or 8.8:1 | 500 mg | 475 | 726 | 448.98 | 51.02 | 5227.2 |
| M | 80:20 or 4:1 | 500 mg | 475 | 754 | 400 | 100 | 5315.7 |
| N | 70:20 or 3.5:1 | 500 mg | 475 | 810 | 388.89 | 111.11 | 5147.5 |
| O | 70:1 | 500 mg | 475 | 769 | 493 | 7 | 5124 |
| P | 60:1 | 500 mg | 475 | 725 | 491.8 | 8.2 | 5200 |
| Q | 50:1 | 500 mg | 475 | 749 | 490.2 | 9.8 | 5284 |
| R | 40:1 | 500 mg | 475 | 737 | 487.8 | 12.2 | 5310 |
| S | 75:25 or 3:1 | 500 mg | 475 | 756 | 375 | 125 | 4158 |
| T | 60:30 or 2:1 | 500 mg | 475 | 742 | 333.3 | 166.6 | 3635.8 |
| U | 50:50 or 1:1 | 500 mg | 475 | 788 | 250 | 250 | 2537 |
| V | 30:60 or 1:2 | 500 mg | 475 | 715 | 166.6 | 333.3 | 1651 |
| W | 25:75 or 1:3 | 500 mg | 475 | 726 | 125 | 375 | 1276 |

Example 5

Comparison of Curcumin Bioavailability from 10:1 and 1:10 Weight Ratios of Curcuminoid Mixture to Essential Oil of Turmeric Nine healthy human volunteers were given four 500 mg capsules having 20 mg curcuminoid mixture without added essential oil of turmeric (referred to as 20 mg C in Table 6). Blood was drawn from the subjects at baseline, 0.5, 1, 1.5, 2, 2.5, 3, 4, 6 and 8 hours post drug. Following one week washout period, the same nine subjects were given four 500 mg capsules having 200 mg of essential oil of turmeric having 10 to 15% Ar-turmerone. Blood was drawn from the subjects at baseline, 0.5, 1, 1.5, 2, 2.5, 3, 4, 6 and 8 hours post drug.

With one week washout period between treatments, the subjects were tested for the following treatments, wherein four of 500 mg capsules were administered to each subject. If any of the capsules had less than 500 mg of the test In another treatment, the capsule had a 10:1 ratio of curcuminoid mixture to added essential oil of turmeric, wherein the essential oil had 45% Ar-turmerone. Each capsule contained 20 mg curcuminoid and 2 mg essential oil of turmeric. The capsule was referred to as 20 mg C: 2 mg E=10:1 (E had 45% Ar-t) in Table 6.

In another treatment, each capsule had curcuminoid mixture without the added essential oil of turmeric. Each capsule contained 454.55 mg curcuminoids. The capsule was referred to as 454.55 mg C without added E in Table 6.

In another treatment, each capsule had essential oil of turmeric having 45% Ar-turmerone. Each capsule contained 45.45 mg essential oil of turmeric. The capsule was referred to as 45.45 mg E (45% Ar-t) in Table 6.

In another treatment, each capsule had curcuminoid mixture along with added essential oil of turmeric with 45% Ar-turmerone at a 10:1 ratio. Each capsule contained 454.55 mg curcuminoids and 45.45 mg of essential oil of turmeric.

The essential oil of turmeric had 45% Ar-turmerone. The capsule was referred to as 454.55 mg C: 45.45 mg E=10:1 (E had 45% Ar-t) in Table 6.

Figure 4:
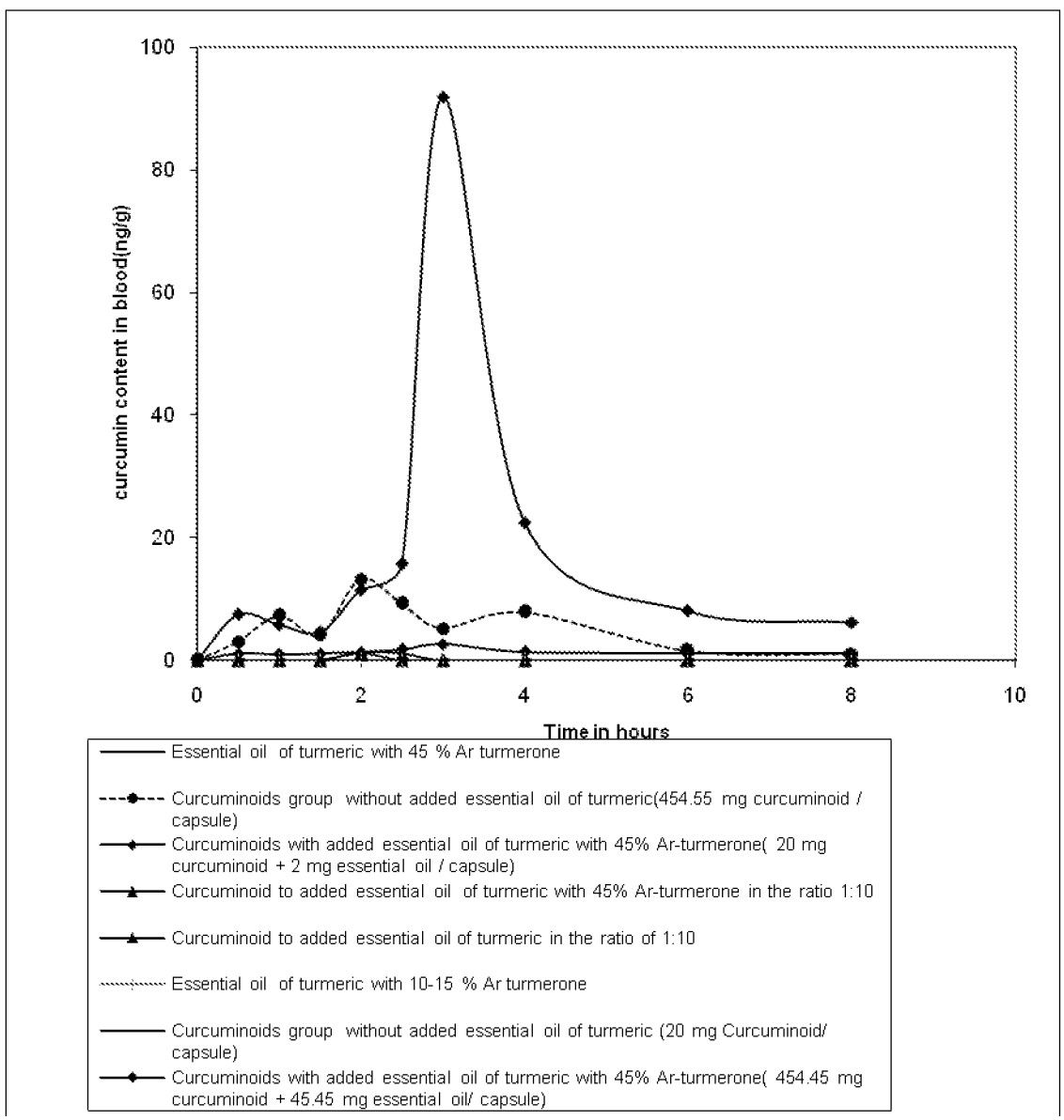
FIG. 4 provides a comparison of curcumin bioavailability from 10:1 and 1:10 weight ratios of 1) curcuminoid (454.55 mg) with added essential oil of turmeric (45.45 mg) with 45% Ar-turmerone in 10:1 ratio, 2) curcuminoid (20 mg) with added essential oil of turmeric (2 mg) with 45% Ar-turmerone in 10:1 ratio, 3) curcuminoid (20 mg) with added essential oil of turmeric (200 mg) with 45% Ar-turmerone in 1:10 ratio, 4) curcuminoid (20 mg) with added essential oil of turmeric (200 mg) with 10-15% Ar-turmerone in 1:10 ratio, 5) curcuminoid alone (454.55 mg), 6) curcuminoid alone (20 mg), 7) Essential oil of turmeric with 45% Ar-turmerone alone (45.45 mg), 8) Essential oil of turmeric with 10-15% Ar-turmerone alone (200 mg). The x-axis shows time in hours and y-axis shows the concentration of curcumin (ng/g) in blood.

Whole blood from the subjects was extracted exhaustively with ethyl acetate to recover curcumin. The ethyl acetate extract was analyzed by HPLC on a RP-C18 column (25×4 5 mm) using tetrahydrofuran (THF) as solvent and UV detection at 420 nm. The eluent flow rate was 1 ml/min. Curcumin content in the blood was determined for each group at each time point and the average value of curcumin in blood (in nanogram per gram of blood) was calculated. The average value of curcumin at each time point for various the treatment protocols was provided in Table 6 and in FIG. 4.

As seen in Table 6, low bioavailability of curcumin of about 1.05 ng curcumin per gm of blood was observed from the negative control having 20 mg of curcuminoid mixture without added essential oil of turmeric. In the negative controls having essential oil of turmeric alone, with either 10-15% Ar-turmerone or 45% Ar-turmerone, the bioavailability of curcumin was not detectable (referred to as Nd in Table 6). Further, bioavailability of curcumin from the capsule prepared and having a 1:10 ratio of curcuminoid mixture to essential oil of turmeric, wherein the essential oil had either a 10-15% Ar-turmerone content or 45% Ar-turmerone content, showed poor bioavailability of curcumin.

An experimental capsule prepared at the ratio of 10:1 of curcuminoid mixture to essential oil of turmeric, wherein the essential oil had a 45% Ar-turmerone content, having 20 mg curcuminoid mixture and 2 mg essential oil of turmeric showed greater than 2-fold enhanced bioavailability over the negative control of 20 mg curcuminoid mixture without the added essential oil of turmeric. On the other hand the positive control having 454.55 mg curcuminoid mixture and 45.55 mg essential oil of turmeric, wherein the essential oil of turmeric had a 45% Ar-turmerone content, i.e., a 10:1 ratio of curcuminoid mixture to essential oil of turmeric, showed a 6.97 fold enhancement of bioavailability of curcumin as compared to the bioavailability of curcumin from the negative control capsule having 454.55 mg curcuminoid mixture without the added essential oil of turmeric.

Example 6

Method of Preparation of Regular Turmeric Extract (95% Curcuminoid Mixture)

The rhizomes of turmeric (300 Kg) were dried. The dried turmeric rhizomes were powdered to form powdered turmeric. The powdered turmeric was treated with ethyl acetate (900 L) to form a solution. The extraction was carried out at 78° C. temperature for 1 hr. After initial extraction, the extraction process was repeated 4 more times and the resultant solution was filtered and the solvent was stripped from the filtered solution to form an extract. This extract was cooled to about 4° C. to obtain crystals of curcuminoid (12 Kg) and a liquid. The crystals of curcuminoid were isolated from the liquid by filtration. The crystals included a mixture of curcumin, demethoxycurcumin and bisdemethoxycurcumin. 95% of the crystals were composed of the mixture of curcumin, demethoxycurcumin and bisdemthoxycurcumin. The crystals were powdered to form powdered curcuminoid mixture. The powdered curcuminoid mixture was also referred to as regular turmeric extract.

A 500 mg capsule containing Regular turmeric extract was prepared by encapsulating the regular turmeric extract in hard gelatin capsules done in an air-conditioned at 21° C. and de-humidified room. 3 kg of powder was charged into the hopper of a semi-automatic capsule filling machine. '0' size hard gelatin capsule shell was loaded to the tray and the powder was filled into the shell. The filled weight of capsules were checked simultaneously and these capsules were sorted by a sorting machine and polished with the help of a polishing machine to give 6000 capsules of 500 mg each.

Example 7

Method of Preparation of Essential Oil of Turmeric with Varying Concentration of Ar-turmerone The rhizomes of turmeric (500 Kg) were dried. The dried turmeric rhizomes were powdered to form powdered turmeric. The powdered turmeric was treated with ethyl acetate (1500 L) to form a solution. The extraction was carried out at 78° C. temperature for 1 hr. After initial extraction, the

TABLE 6

Comparison of curcumin bioavailability from 10:1 and 1:10 weight ratios of curcuminoid mixture to essential oil of turmeric.

| | Nanograms of curcumin per gram of blood | | | | | | | |
|---|---|---|---|---|---|---|---|---|
| Time (h) | 20 mg C | 200 mg E alone (10-15% Ar-t) | 20 mg C: 200 mg E = 1:10 (E had 10-15% Ar-t) | 20 mg C: 200 mg E = 1:10 (E had 45% Ar-t) | 20 mg C: 2 mg E = 10:1, (E had 45% Ar-t) | 454.55 mg C without added E | 45.45 mg E (45% Ar-t) | 454.55 mg C: 45.45 mg E = 10:1 (E had 45% Ar-t) |
| 0 | 0 | 0 | 0 | 0 | 0 | 0 | 0 | 0 |
| 0.5 | Nd | Nd | Nd | Nd | 1.1 | 3.02 | Nd | 7.45 |
| 1 | Nd | Nd | Nd | Nd | 1 | 7.27 | Nd | 5.81 |
| 1.5 | Nd | Nd | Nd | Nd | 1.05 | 4.11 | Nd | 4.52 |
| 2 | 1.05 | Nd | 1.1 | 1.3 | 1.3 | 13.18 | Nd | 11.46 |
| 2.5 | Nd | Nd | Nd | 1.1 | 1.7 | 9.17 | Nd | 15.66 |
| 3 | Nd | Nd | Nd | Nd | 2.67 | 5.21 | Nd | 91.9 |
| 4 | Nd | Nd | Nd | Nd | 1.34 | 7.82 | Nd | 22.44 |
| 6 | Nd | Nd | Nd | Nd | 1.1 | 1.54 | Nd | 8.01 |
| 8 | Nd | Nd | Nd | Nd | 1.05 | 1.05 | Nd | 6.18 | extraction process was repeated 4 more times and the resultant solution was filtered and the solvent was stripped from the filtered solution to form an extract. This extract was cooled to about 4° C. to obtain crystals of curcuminoid (20 Kg) and a liquid. The crystals of curcuminoid were isolated from the liquid by filtration.

Figure 5:
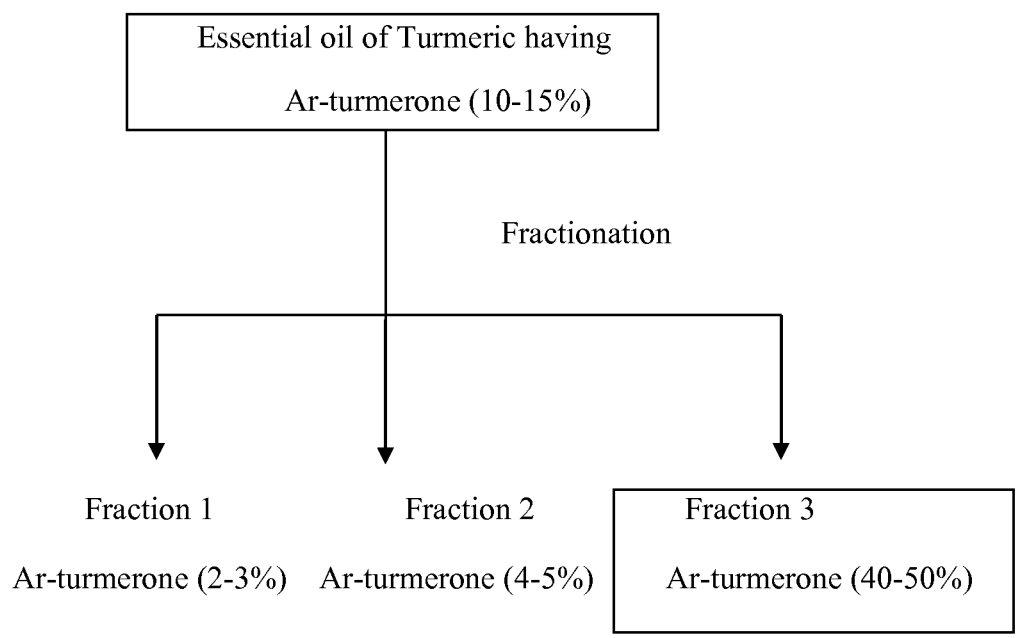
FIG. 5 provides Method of preparation of Essential oil of turmeric having varying concentration of Ar-turmerone.

The remaining liquid includes the essential oil of turmeric and a resin. The liquid was then steam distilled to isolate essential oil of turmeric with 10-15% Ar turmerone (25 Kg). After fractionating this oil, essential oil with 45% Ar turmerone (7.5 Kg) was obtained as fraction 3, essential oil of turmeric with 4-5% Ar turmerone (8.3) was obtained as fraction 2 and essential oil of turmeric with 2-3% Ar turmerone (9.3 Kg) was obtained as fraction 1. Flow chart was provided in FIG. 5.

Example 8

Method of Preparation of Combination of Curcuminoids and Essential Oil of Turmeric with 45% Ar-turmerone in 10:1 Ratio The curcuminoid powder prepared as per Example 6 (2.7 Kg) was suspended in water (12 L) to form a suspension. Fraction of essential oil containing 45% Ar-turmerone prepared as per Example 7(0.27 Kg) was added to the suspension in 10:1 ratio. The mixture was pulverized in a colloidal mill to form fine slurry. Water was stripped from the slurry under heat and vacuum to form a uniform blend (3 Kg) having curcuminoid mixture and essential oil containing 45% Ar-turmerone.

A 500 mg capsule containing 454.55 mg of curcuminoid and 45.45 mg of Essential oil with 45% Ar-turmerone in a weight ratio of about 90:9 (10:1) was prepared by encapsulating the above blended extract powder in hard gelatin capsules done in an air-conditioned at 21° C. and de-humidified room. 3 kg of extract powder was charged into the hopper of a semi-automatic capsule filling machine. '0' size hard gelatin capsule shell was loaded to the tray and the blended extract powder was filled into the shell. The filled weight of capsules were checked simultaneously and these capsules were sorted by a sorting machine and polished with the help of a polishing machine to give 6000 capsules of 500 mg each.

Example 9

Method of Preparation of Combination of Curcuminoids and Essential Oil of Turmeric with 45% Ar-turmerone in 1:10 Ratio The curcuminoid powder prepared as per Example 6 (0.27 Kg) was suspended in water (1 L) to form a suspension. Fraction of essential oil containing 45% Ar-turmerone prepared as per Example 7 (2.7 Kg) was added to the suspension in 1:10 ratio. The mixture was pulverized in a colloidal mill to form fine slurry. Water was stripped from the slurry under heat and vacuum to form a uniform blend (3 Kg) having curcuminoid mixture and essential oil containing 45% ar-turmerone.

Capsule containing curcuminoid and Essential oil of turmeric with 45% Ar-turmerone in a weight ratio of about 1:10 was prepared by encapsulating the above blended extract powder in soft gelatin capsules done in an air-conditioned at 21° C. and de-humidified room. 3 kg of extract powder was charged into the hopper of a semi-automatic capsule filling machine. '0' size soft gelatin capsule shell was loaded to the tray and the blended extract powder was filled into the shell. The filled weights of capsules were checked simultaneously and these capsules were sorted by a sorting machine and polished with the help of a polishing machine.

Example 10

Method of Preparation of Combination of Curcuminoids and Essential Oil of Turmeric with 45% Ar turmerone in 1:1 Ratio The curcuminoid powder prepared as per Example 6 (1.5 Kg) was suspended in water (6 L) to form a suspension. Fraction of essential oil containing 45% Ar-turmerone prepared as per Example 7(1.5 Kg) was added to the suspension in 1:1 ratio. The mixture was pulverized in a colloidal mill to form fine slurry. Water was stripped from the slurry under heat and vacuum to form a uniform blend (3 Kg) having curcuminoid mixture and essential oil containing 45% Ar-turmerone.

A 500 mg capsule containing 250 mg of curcuminoid and 250 mg of Essential oil of turmeric with 45% Ar-turmerone in a weight ratio of about 1:1 was prepared by encapsulating the above blended extract powder in hard gelatin capsules done in an air-conditioned at 21° C. and de-humidified room. 3 kg of extract powder was charged into the hopper of a semi-automatic capsule filling machine. '0' size hard gelatin capsule shell was loaded to the tray and the blended extract powder was filled into the shell. The filled weight of capsules were checked simultaneously and these capsules were sorted by a sorting machine and polished with the help of a polishing machine to give 6000 capsules of 500 mg each.

Example 11

Method of Preparation of Combination of Curcuminoids and Essential Oil of Turmeric with 10-15% Ar-turmerone in 10:1 Ratio The curcuminoid powder prepared as per Example 6 (2.7 Kg) was suspended in water (12 L) to form a suspension. Fraction of essential oil of turmeric containing 10-15% Ar-turmerone prepared as per Example 7 (0.27 Kg) was added to the suspension in 10:1 ratio. The mixture was pulverized in a colloidal mill to form fine slurry. Water was stripped from the slurry under heat and vacuum to form a uniform blend (3 Kg) having curcuminoid mixture and essential oil containing 45% ar-turmerone.

A 500 mg capsule containing 454.55 mg of curcuminoid and 45.45 mg of Essential oil of turmeric with 10-15% Ar-turmerone in a weight ratio of about 90:9 (10:1) was prepared by encapsulating the above blended extract powder in hard gelatin capsules done in an air-conditioned at 21° C. and de-humidified room. 3 kg of extract powder was charged into the hopper of a semi-automatic capsule filling machine. '0' size hard gelatin capsule shell was loaded to the tray and the blended extract powder was filled into the shell. The filled weight of capsules were checked simultaneously and these capsules were sorted by a sorting machine and polished with the help of a polishing machine to give 6000 capsules of 500 mg each.

Example 12

Method of Analysis of Total Curcuminoids by HPLC Method

From 500 mg capsule, 25 mg was accurately weighed and transferred into a 50 ml standard flask and made up to a 50 ml solution with methanol. From this pipette out 2 ml into 50 ml standard flask and made up to a 50 ml solution with methanol. Filter through 0.2 μm membrane filter before injection. Standard was prepared by weighing accurately 25 mg standard [Curcumin Standard: 99% Total Curcuminoids (Sigma)] and transferred into a 50 ml standard flask and made up to a 50 ml solution with methanol. From this pipette out 2 ml into 50 ml standard flask and made up to a 50 ml solution with methanol. Filter through 0.2 μm membrane filter before injection.

The total Curcuminoids was analyzed by high performance liquid chromatography (HPLC) on a C18 column ((250λ4.6 mm Shimadzu Co., Japan.) using tetrahydrofuran (THF) as the mobile phase and UV detection at 420 nm. The eluent flow rate was 1 ml/min.

By comparing the area of standard and sample, the percentage of total curcuminoids was calculated using the formula $$\% \text{ of total Curcuminoid} = \frac{\text{Area of sample} \times \text{amount of std} \times \text{Purity of std}}{\text{Area of Std} \times \text{weight of the sample}}$$

Example 13

Method of Manufacture of Placebo Capsules 10 kgs of raw rice was washed well and roasted in a rotatory paddle type roaster. The roasted rice (9.5 kg) was powdered and sterilized under controlled temperature which was passed through 30 mesh sieve to obtain fine powder of roasted rice.

A 500 mg placebo capsule containing 500 mg of a powder of roasted rice was prepared by encapsulating the powder in hard gelatin capsules. The process was performed in an air-conditioned at 21° C. and de-humidified room. 2 kg of powder was charged into the hopper of a semi-automatic capsule filling machine. '0' size hard gelatin capsule shell was loaded to the tray and the extract powder was filled into the shell. The filled weight of capsules were checked simultaneously and these capsules were sorted by a sorting machine and polished with the help of a polishing machine to give 4000 placebo capsules of 500 mg each.

Example 14

Method of Preparation of Raw Turmeric Powder

Fresh turmeric rhizomes (10 Kg) were collected and cleaned. The rhizomes were dried and pulverized to get turmeric powder (2.5 Kg). The turmeric powder was sieved through 20 meshes to obtain raw turmeric powder. The raw turmeric powder contained curcuminoids in the amount of 5% weight/weight. A 500 mg capsule with raw turmeric powder was prepared by encapsulating the powder in hard gelatin capsules. Encapsulation was performed in an air-conditioned at 21° C. and de-humidified room. 2.5 kg raw turmeric powder was charged into the hopper of a semi-automatic capsule filling machine. '0' size hard gelatin capsule shell was loaded to the tray and the blended extract powder was filled into the shell. The filled weight of capsules were checked simultaneously and these capsules were sorted by a sorting machine and polished with the help of a polishing machine to give 5000 capsules having 500 mg each of raw turmeric powder.

Example 15

Method of Preparation of Combination of Curcuminoids and Essential Oil of Turmeric with 45% Ar Turmerone in 12:1 Ratio The curcuminoid powder prepared as per Example 6 (3.5 Kg) was suspended in water (15 L) to form a suspension. Fraction of essential oil containing 45% Ar-turmerone prepared as per Example 7 (0.29 Kg) was added to the suspension in 12:1 ratio. The mixture was pulverized in a colloidal mill to form fine slurry. Water was stripped from the slurry under heat and vacuum to form a uniform blend. (3.8 Kg).

A 500 mg capsule containing 461.5 mg of curcuminoid and 38.45 mg of Essential oil with 45% Ar-turmerone in a weight ratio of about 12:1 was prepared by encapsulating the above blended extract powder in hard gelatin capsules done in an air-conditioned at 21° C. and de-humidified room. 3 kg of extract powder was charged into the hopper of a semi-automatic capsule filling machine. '0' size hard gelatin capsule shell was loaded to the tray and the blended extract powder was filled into the shell. The filled weight of capsules were checked simultaneously and these capsules were sorted by a sorting machine and polished with the help of a polishing machine to give 6000 capsules of 500 mg each.

Example 16

Clinical Effectiveness of Curcuminoids with Turmeric Essential Oil Combination

Figure 6:
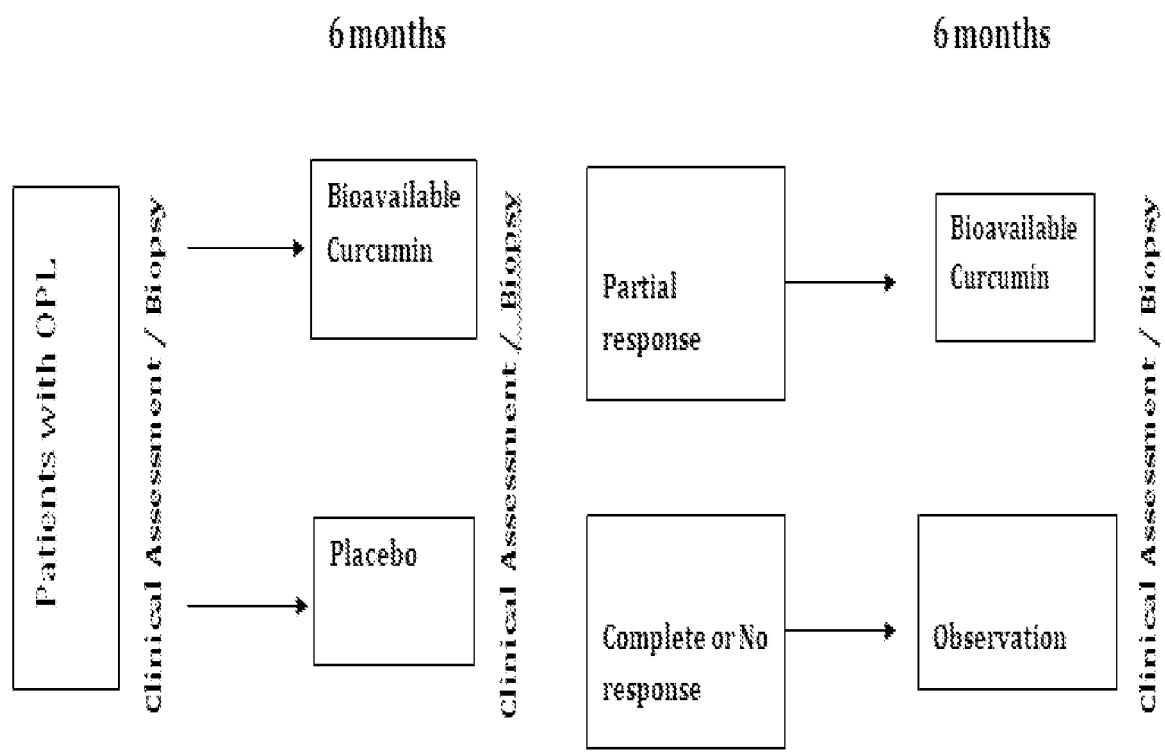
FIG. 6 shows a pilot double blind, placebo controlled clinical trial to determine the clinical efficacy and safety of curcuminoid with essential oil of turmeric in oral premalignant lesions.

A pilot double blind, placebo controlled clinical trial was carried out to determine the clinical efficacy and safety of curcuminoid with essential oil of turmeric in oral premalignant lesions (FIG. 6).

Curcuminoids blended with essential oil of turmeric having 45% Ar-turmerone in 12:1 ratio (bioenhanced formulation) were packaged in gelatin capsules of 500 mg each. Subjects were orally administered a dosage of one 500 mg capsule thrice daily.

40 subjects with oral premalignant lesions were enrolled after signing informed consent. After initial biopsy, subjects were randomized to either bioenhanced formulation 1.5 g/day or placebo cap thrice daily for six months. At the end of six months of treatment the lesion were measured for the primary assessment of clinical and pathologic response. Those patients with clinical partial response were continued on the bioenhanced formulation therapy for another six months. The other patients were followed for six more months to assess the durability of the response.

34 subjects completed the study with 6 subjects dropped out from the placebo group. The compliance to drug was 90%. No subjects showed any untoward toxicity to the medication. One serious adverse event (SAE) and twelve adverse events (AE) were reported. There were no correlations of AEs and SAEs to the study drug.

Biomarker assay included estimation of NF-kB, COX-2, IL-6, CRP, PCNA (Proliferating Cell Nuclear Antigen) and TUNEL assay. There was significant reduction in NF-kB by IHC (immunohistochemistry) and COX-2 by PCR expression in the experimental group of subjects taking capsules comprising a composition having curcuminoids with essential oil of turmeric with 45% Ar-t in 12:1 ratio. Clinically both karnofsky performance status and ECOG scale showed significant improvement.

This study concludes that curcuminoids with essential oil of turmeric with 45% Ar-t is an effective anticancer medication in head and neck tumors.

The following table 7 & 8 describes the Karnofsky scale and ECOG/Zubrod score.

TABLE 7

Karnofsky Performance Status Scale Definitions Rating (%) Criteria

| | | |
|---|---|---|
| Able to carry on normal activity and to work No special care needed | 100 90 80 | Normal; no complaints; no evidence of disease Able to carry on normal activity; minor signs or symptoms of disease Normal activity with effort; some signs or symptoms of disease |
| Unable to work Able to live at home and care for most personal needs Varying amount of assistance needed | 70 60 50 | Cares for self; unable to carry on normal activity or to do active work Requires occasional assistance but is able to care for most of own personal needs Requires considerable assistance and frequent medical care |
| Unable to care for self Requires equivalent of institutional or hospital care Disease may be progressing rapidly | 40 30 20 10 0 | Disabled; requires special care and assistance Severely disabled; hospital admission is indicated although death not imminent Very sick; hospital admission necessary; active supportive treatment necessary Moribund; fatal processes progressing Dead |

TABLE 8

ECOG/WHO/Zubrod score
ECOG/WHO/Zubrod score

0 Asymptomatic. (Fully active, able to carry on all pre disease activities without restriction).
1 Symptomatic but completely ambulatory. (Restricted in physically strenuous activity but ambulatory and able to carry out work of a light or sedentary nature. For example, light housework, office work).
2 Symptomatic, <50% in bed during the day. (Ambulatory and capable of all self care but unable to carry out any work activities. Up and about more than 50% of waking hours).
3 Symptomatic, >50% in bed, but not bedbound. (Capable of only limited self-care, confined to bed or chair 50% or more of waking hours).
4 Bedbound. (Completely disabled. Cannot carry on any self-care. Totally confined to bed or chair).
5 Death

TABLE 9

Biochemical parameters and Performance scales in patients treated with placebo and bioenhanced formulation.

| | | Patients administered curcuminoids with essential oil of turmeric with 45% Ar-t in 12:1 | | Patients administered Placebo | |
|---|---|---|---|---|---|
| S.N | Parameter | Before | After | Before | After |
| 1 | COX-2 (ng/ml) | 26.4 | 12.5 | 22.8 | 20.6 |
| 2 | IL-6 (pg/ml) | 8.6 | 4.3 | 8.3 | 8.1 |
| 3 | CRP (mg/L) | 10.6 | 6.3 | 11.2 | 10.3 |
| 4 | Karnofsky Performance Status (KPS) Scale | 38.2 | 78.6 | 35.4 | 32.1 |
| 5 | ECOG/Zubrod Scale | 3.36 | 2.08 | 3.54 | 3.51 |

Results indicate a significant reduction in COX-2, IL6, and CRP levels in patients taking capsules comprising a composition having curcuminoids with essential oil of turmeric with 45% Ar-t in 12:1 ratio as compared to the patients taking placebo. Results also showed a decrease in the ECOG/Zubrod Scale and increase in Karnofsky Score in the patients taking capsules comprising a composition having curcuminoids with essential oil of turmeric with 45% Ar-t in 12:1 ratio. There was not significant change in ECOG/Zubrod Scale and Karnofsky Score in the patients taking placebo.

Out of the 40 subjects, in the bio enhanced formulation group 20 subjects were completed the study and in the placebo group 14 subjects completed the study with 6 subjects dropped out from the placebo group.

TABLE 10

Clinical and pathological response in patients treated with placebo and bioenhanced formulation.

| Parameters | Patients administered curcuminoids with essential oil of turmeric with 45% Ar-t in 12:1 | Patients administered Placebo |
|---|---|---|
| Number of patients with transformation of oral premalignant to malignant lesion | Nil | 8 |
| Number of patients with increase in degree of epithelial dysplasia of oral premalignant lesions | Nil | 10 |
| Number of patients with decrease in degree of epithelial dysplasia of oral premalignant lesions | 20 | 2 |
| Number of patients with reduction in tumor size of oral premalignant lesions | 18 | 1 |
| Number of patients with improvement in quality of life | 20 | 5 |
| Number of patients with decrease in Nuclear factor kappa B (NF-kB) | 19 | 1 |

Patients with oral premalignant lesion after taking capsules comprising a composition having curcuminoids with essential oil of turmeric with 45% Ar-t in 12:1 ratio had a significant reduction in tumor size, reduced the transformation of oral premalignant to malignant lesion, significant reduction in Nuclear factor kappa B (NF-kB) by IHC (immunohistochemistry) and improvement in degree of epithelial dysplasia compared to the patients taking placebo. The quality of life and symptoms of patients with oral premalignant lesion were assessed by Karnofsky scale, ECOG/Zubrod scale. The improvement in quality of life and reduction of symptoms were evidenced by improvement in the Karnofsky scale and ECOG/Zubrod scale. The quality of life and symptoms of patients with oral premalignant lesion taking capsules comprising a composition having curcuminoids with essential oil of turmeric with 45% Ar-t in 12:1 ratio is significantly improved as compared to the patients taking placebo.

Example 17

Bioavailability Study Using Curcuminoids with Different Fractions of Ar-turmerone Albino rats weighing 200-250 gm of both sexes were used for the study. The rats were kept individually in polypropylene cages and maintained in well ventilated room under normal and uniform conditions like 12 hours light and dark cycle and at 26±2° C. Water and feed were given ad-libitum.

The animals were divided into 8 groups and 3 animals were used for each group. The groups are provided in Table 11.

TABLE 11

Segregation of rats for experimental study.

| Group 1 | Control (Tween 80) Dose: 60 mg/Kg.body wt. |
|---|---|
| Group 2 | Regular turmeric extract Dose: 60 mg/Kg body wt. |
| Group 3 | Curcuminoid mixture blended with essential oil of turmeric having 20% Ar-turmerone in 12:1 ratio. Dose: 60 mg/Kg body wt.. |
| Group 4 | Curcuminoid mixture blended with essential oil of turmeric having 30% Ar-turmerone in 12:1 ratio. Dose: 60 mg/Kg body wt. |
| Group 5 | Curcuminoid mixture blended with essential oil of turmeric having 40% Ar-turmerone in 12:1 ratio. Dose: 60 mg/Kg body wt. |
| Group 6 | Curcuminoid mixture blended with essential oil of turmeric having 45% Ar-turmerone in 12:1 ratio. Dose: 60 mg/Kg body wt. |
| Group 7 | Curcuminoid mixture blended with essential oil of turmeric having 50% Ar-turmerone in 12:1 ratio. Dose: 60 mg/Kg body wt. |
| Group 8 | Curcuminoid mixture blended with essential oil of turmeric having 60% Ar-turmerone in 12:1 ratio. Dose: 60 mg/Kg body wt. |

The animals were able to access drinking water freely. The study drugs were given by oral route. Two hours post drug the blood was collected for analysis of curcumin levels in the blood by HPLC method. The blood was extracted exhaustively with ethyl acetate to recover curcumin. The ethyl acetate extract was analyzed by HPLC on a RP-C18 column (250×4 5 mm) using tetrahydrofuran (THF) as solvent and UV detection at 420 nm. The eluent flow rate was 1 ml/min.

TABLE 12

Bioavailability of curcumin in rats by administering curcuminoids with different fractions of Ar-turmerone.

| Groups | Treatment | Curcumin content in ng/g |
|---|---|---|
| Group 1 | Control (Tween 80) | ND |
| Group 2 | Regular turmeric extract | 5.3 |
| Group 3 | Curcuminoid mixture with essential oil of turmeric having 20% Ar-turmerone in 12:1 ratio | 11.4 |
| Group 4 | Curcuminoid mixture with essential oil of turmeric having 30% Ar-turmerone in 12:1 ratio | 20.6 |
| Group 5 | Curcuminoid mixture with essential oil of turmeric having 40% Ar-turmerone in 12:1 ratio | 32.5 |
| Group 6 | Curcuminoid mixture with essential oil of turmeric having 45% Ar-turmerone in 12:1 ratio | 57.8 |
| Group 7 | Curcuminoid mixture with essential oil of turmeric having 50% Ar-turmerone in 12:1 ratio | 57.5 |
| Group 8 | Curcuminoid mixture with essential oil of turmeric having 60% Ar-turmerone in 12:1 ratio | 57.7 |

Results are provided in Table 12. Animals fed with curcuminoid mixture blended with essential oil of turmeric having 45% Ar-turmerone showed 10.9 times enhanced curcumin bioavailability compared to regular turmeric extract. Animals fed with curcuminoid mixture blended with essential oil of turmeric having 50% Ar-turmerone showed 10.8 times bioavailability of curcumin compared to regular turmeric extract. Animals fed with curcuminoid mixture blended with essential oil of turmeric having 60% showed 10.8 times bioavailability of curcumin compared to regular turmeric extract. Animals fed with regular turmeric extract (Group 2) shows very low detection of curcumin in blood. Animals fed with curcuminoid mixture blended with essential oil of turmeric having 20% Ar-turmerone showed 2.2 times bioavailability of curcumin compared to regular turmeric extract. Animals fed with curcuminoid mixture blended with essential oil of turmeric having 30% Ar-turmerone showed 3.8 times bioavailability of curcumin compared to regular turmeric extract. Animals fed with curcuminoid mixture blended with essential oil of turmeric having 40% Ar-turmerone showed 6.1 times bioavailability of curcumin compared to regular turmeric extract.

What is claimed is:

1. A method of treating premalignant lesions of the head and neck in a subject in need thereof, the method comprising administering to the subject an effective amount of a composition that enhances bioavailability of curcumin, the composition comprising a curcuminoid mixture and an essential oil of turmeric, wherein the curcuminoid mixture consists of curcumin, demethoxycurcumin and bisdemethoxycurcumin, and the essential oil of turmeric comprises about 45% ar-turmerone, wherein the weight ratio of the curcuminoid mixture to the essential oil of turmeric ranges from about 1:3 to about 99:1, and wherein the enhanced bioavailability of curcumin in the subject ranges from more than 2 fold to about 16 fold.

2. A method of decreasing the size of premalignant lesions of the head and neck in a subject in need thereof, the method comprising administering to the subject an effective amount of a composition that enhances bioavailability of curcumin, the composition comprising a curcuminoid mixture and an essential oil of turmeric, wherein the curcuminoid mixture consists of curcumin, demethoxycurcumin and bisdemethoxycurcumin, and the essential oil of turmeric comprises about 45% ar-turmerone, wherein the weight ratio of the curcuminoid mixture to the essential oil of turmeric ranges from about 1:3 to about 99:1, and wherein the enhanced bioavailability of curcumin in the subject ranges from more than 2 fold to about 16 fold.

3. A method of inhibiting malignant transformation of premalignant lesions of the head and neck in a subject in need thereof, the method comprising administering to the subject an effective amount of a composition that enhances bioavailability of curcumin, the composition comprising a curcuminoid mixture and an essential oil of turmeric, wherein the curcuminoid mixture consists of curcumin, demethoxycurcumin and bisdemethoxycurcumin, and the essential oil of turmeric comprises about 45% ar-turmerone, wherein the weight ratio of the curcuminoid mixture to the essential oil of turmeric ranges from about 1:3 to about 99:1, and wherein the enhanced bioavailability of curcumin in the subject ranges from more than 2 fold to about 16 fold.

4. A method of inhibiting the occurrence of premalignant lesions in the head and neck in a subject in need thereof, the method comprising administering to the subject an effective amount of a composition that enhances bioavailability of curcumin, the composition comprising a curcuminoid mixture and an essential oil of turmeric, wherein the curcuminoid mixture consists of curcumin, demethoxycurcumin and bisdemethoxycurcumin, and the essential oil of turmeric comprises about 45% ar-turmerone, wherein the weight ratio of the curcuminoid mixture to the essential oil of turmeric ranges from about 1:3 to about 99:1, and wherein the enhanced bioavailability of curcumin in the subject ranges from more than 2 fold to about 16 fold.

5. A method of improving quality of life in a patient with head and neck premalignant lesions, the method comprising administering to the patient an effective amount of a composition that enhances bioavailability of curcumin, the composition comprising a curcuminoid mixture and an essential oil of turmeric, wherein the curcuminoid mixture consists of curcumin, demethoxycurcumin and bisdemethoxycurcumin, and the essential oil of turmeric comprises about 45% ar-turmerone, wherein the weight ratio of the curcuminoid mixture to the essential oil of turmeric ranges from about 1:3 to about 99:1, and wherein the enhanced bioavailability of curcumin in the patient ranges from more than 2 fold to about 16 fold.

6. A method of decreasing symptoms associated with head and neck oral premalignant lesions in a subject in need thereof, the method comprising administering to the subject an effective amount of a composition that enhances bioavailability of curcumin, the composition comprising a curcuminoid mixture and an essential oil of turmeric, wherein the curcuminoid mixture consists of curcumin, demethoxycurcumin and bisdemethoxycurcumin, and the essential oil of turmeric comprises about 45% ar-turmerone, wherein the weight ratio of the curcuminoid mixture to the essential oil of turmeric ranges from about 1:3 to about 99:1, and wherein the enhanced bioavailability of curcumin in the subject ranges from more than 2 fold to about 16 fold.

7. A method of treating oral premalignant lesions in a subject in need thereof, the method comprising administering to the subject an effective amount of a composition that enhances bioavailability of curcumin, the composition comprising a curcuminoid mixture and an essential oil of turmeric, wherein the curcuminoid mixture consists of curcumin, demethoxycurcumin and bisdemethoxycurcumin, and the essential oil of turmeric comprises about 45% ar-turmerone, wherein the weight ratio of the curcuminoid mixture to the essential oil of turmeric ranges from about 1:3 to about 99:1, wherein the composition is orally administered in a dosage of about 500 mg/dose three times daily, and wherein the enhanced bioavailability of curcumin in the subject ranges from more than 2 fold to about 16 fold.

8. The method of treating premalignant lesions of claim 1, wherein the composition is orally administered at a dosage of about 500 mg/dose three times daily for six months.

* * * * *